(12) United States Patent
Cushman et al.

(10) Patent No.: US 7,312,228 B2
(45) Date of Patent: Dec. 25, 2007

(54) CYTOTOXIC INDENO AND ISOINDOLOISOQUINOLONES

(75) Inventors: Mark S. Cushman, West Lafayette, IN (US); Yves G. Pommier, Bethesda, MD (US)

(73) Assignees: Purdue Research Foundation, West Lafayette, IN (US); The United States of America as represented by the Secretary of the Department of Health and Human Services, Washington, DC (US)

( * ) Notice: Subject to any disclaimer, the term of this patent is extended or adjusted under 35 U.S.C. 154(b) by 0 days.

(21) Appl. No.: 10/553,532

(22) PCT Filed: May 11, 2004

(86) PCT No.: PCT/US2004/014581

§ 371 (c)(1),
(2), (4) Date: Oct. 14, 2005

(87) PCT Pub. No.: WO2004/100891

PCT Pub. Date: Nov. 25, 2004

(65) Prior Publication Data

US 2006/0247211 A1    Nov. 2, 2006

Related U.S. Application Data

(60) Provisional application No. 60/469,718, filed on May 12, 2003.

(51) Int. Cl.
*A61K 31/473* (2006.01)
*C07D 491/02* (2006.01)

(52) U.S. Cl. ................ 514/280; 546/48; 546/61; 514/284

(58) Field of Classification Search ............... 514/280, 514/284; 546/48, 61
See application file for complete search history.

(56) References Cited

U.S. PATENT DOCUMENTS

| 5,597,831 | A | 1/1997 | Michalsky et al. |
| 6,509,344 | B1 | 1/2003 | Cushman et al. |
| 6,828,319 | B2 * | 12/2004 | Jagtap et al. ............ 514/232.8 |

FOREIGN PATENT DOCUMENTS

| WO | WO 97/43290 | 11/1997 |
| WO | 200021537 | 4/2000 |
| WO | WO 00/21537 | 4/2000 |
| WO | WO 01/30753 A2 | 5/2001 |
| WO | 03051289 | 6/2003 |
| WO | 2004014862 | 2/2004 |
| WO | 2004014906 | 2/2004 |
| WO | 2004014918 | 2/2004 |

OTHER PUBLICATIONS

Lal, B. et al.: Applications of carbon-nitrogen bond cleavage reaction : a synthesis/derivatization of 11H-indeno[1,2-c]isoquinolines. Indian J. Chem. , Sec. B, vol. 38B, pp. 33-39, 1999.*

Gomes, L.M. et al.: New methodology for the preparation of the indeno[1,2-c]isoquinoline derivatives. Comptes rendus de l' Academie des Sciences, Serie II, vol. 310, pp. 1431-1435, 1990.*

Antony et al., "Differential Induction of Topoisomerase I-DNA Cleavage Complexes by the Indenoisoquinoline MJ-III-65 (NSC 706744) and Camptothecin: Base Sequence Analysis and Activity Against Camptothecin-Resistant Topoisomerase I," Cancer Res., 2003, vol. 63, pp. 7428-7435.

Antony et al., "Cellular Topoisomerase I Inhibition and Antiproliferative Activity by MJ-III-65 (NSC 706744), an Indenoisoquinoline Topoisomerase I Poison," Molecular Pharmacology, 2005, vol. 67, No. 2, 523-530.

Canan Koch et al., "Enantioselective Preparation of B-Alkyl-γ-butyrolactones from Functionalized Ketene Dithioacetals," J. Org. Chem., 1993, vol. 58, No. 10, 2725-2737.

Corey et al., "A Total Synthesis of Natural 20(S)-Camptothecin," J. Org. Chem., vol. 40, No. 14, 1975, pp. 2140-2141.

Cushman et al., "Stereoselective Oxidation by Thionyl Chloride Leading to the Indeno[1,2-c]isoquinoline System," J. Org. Chem., 1978, vol. 43, No. 19, pp. 3781-3783.

Cushman et al., "Synthesis and Antitumor Activity of Structural Analogues of the Anticancer Benzophenanthridine Alkaloid Fagaronine Chloride," J. Med. Chem., 1985, vol. 28, No. 8, pp. 1031-1036.

Cushman et al., "Synthesis and Biological Activity of Structural Analogues of the Anticancer Benzophenanthridine Alkaloid Nitidine Chloride," J. Med. Chem., 1984, vol. 27, No. 4, 544-547.

Cushman et al., "Synthesis of New Indeno[1,2-c]isoquinolines: Cytotoxic Non-Camptothecin Topoisomerase I Inhibitors," J. Med. Chem., 2000, vol. 43, No. 20, pp. 3688-3698.

Cushman et al., "Total Synthesis of Nitidine Chloride," J. Org. Chem., 1978, vol. 43, No. 2, pp. 286-288.

Hertzberg et al., "On the Mechanism of Topoisomerase I Inhibition by Camptothecin: Evidence for Binding to an Enzyme-DNA Complex," Biochemistry, 1989, vol. 28, No. 11, 4629-4638.

Hertzberg et al., "Modification of the Hydroxy Lactone Ring of Camptothecin: Inhibition of Mammalian Topoisomerase I and biological Activity," J. Med. Chem., 1989, vol. 32, No. 3, 715-720.

Ioanoviciu et al., "Synthesis and Mechanism of Action Studies of a Series of Norindenoisoquinoline Topoisomerase I Poisons Reveal an Inhibitor with a Flipped Orientation in the Ternary DNA-Enzyme-Inhibitor Complex As Determined by X-ray Crystallographic Analysis," J. Med. Chem., 2005, vol. 48, No. 15, 4803-4814.

(Continued)

*Primary Examiner*—Charanjit S. Aulakh
(74) *Attorney, Agent, or Firm*—Barnes & Thornburg LLP

(57) ABSTRACT

The synthesis and biological activity of benzoisoindoloisoquinolone compounds are described. The synthesis and biological activity of C-11-substituted indenoisoquinolones are also described. Indenoisoquinolones substituted at C-11 are prepared by McMurry reactions of 11-ketoindenoisoquinolones with aldehydes.

19 Claims, 4 Drawing Sheets

OTHER PUBLICATIONS

Jayaraman et al., "Novel Oxidative Transformation of Indenoisoquinolines to Isoquinoline-3-spiro-3'-phthalides in the Presence of Osmium Tetraoxide and 4-methylmorpholine N-Oxide," J. Org. Chem., 1998, vol. 63, No. 17, 5736-5737.

Jayaraman et al., "Synthesis of New Dihydroindeno[1,2-c]isoquinoline and Indenoisoquinolinium Chloride Topoisomerase I Inhibitors Having High In Vivo Anticancer Activity in the Hollow Fiber Animal Model," J. Med. Chem., 2002, vol. 45, No. 1, pp. 242-249.

Kohlhagen et al., "Protein-Linked DNA Strand Breaks Induced by NSC 314622, a Novel Noncamptothecin Topoisomerase I Poison," Mol. Pharmacol., 1998, vol. 54, pp. 50-58.

Kubova et al., "Binding Properties of Nitidine and Its Indenoisoquinoline Analogue wth DNA," Studia Biophs., 1986, vol. 114, No. 1-3, pp. 251-256.

Li et al., "Synthesis of the Tricyclic ABC Ring Subunit of Mazamine A," Tetrahedron, vol. 54 (1998), 6661-6676.

Morrell et al., "Synthesis of nitrated indenoisoquinoles as topoisomerase I inhibitors," Bioorganic & Medicinal Chemistry Letters, vol. 14 (2004), 3659-3663.

Nagarajan et al., "Design, Synthesis, and Biological Evaluation of Indenoisoquinoline Topoisomerase I Inhibitors Featuring Polyamine Side Chains on the Lactam Nitrogen," J. Med. Chem., 2003, vol. 46, No. 26, pp. 5712-5724.

Nagarajan et al., "Synthesis and Anticancer Activity of Simplified Indenoisoquinoline Topoisomerase I Inhibitors Lacking Substituents on the Aromatic Rings," J. Med. Chem., 2004, vol. 47, No. 23, pp. 5651-5661.

Patel et al., "Neuromuscular blocking activity of bis-4-benzyltetrahydroisoquinolinium esters in the cat," European Journal of Pharmaceutical Sciences, vol. 4 (1996), 63-71.

Pommier et al, Editorial Overview "Topoisomerase Inhibitors: Why New Ones?", Opinion in Oncologic, Endocrine & Metabolic Investigational Drugs, 1(2), 168-169 (1999).

Pommier et al., "Mechanism and action of eukaryotic DNA topoisomerase I and drugs targeted to the enzyme," Biochem. Biophys. Acta., 1400, 83-106 (1998).

Pourquier et al., "Induction of Reversible Complexes between Eukaryotic DNA Topoisomerase I and DNA-containing Oxidative Base Damages," The Journal of Biological Chemistry, vol. 274, No. 13, 1999, pp. 8516-8523.

Shetty et al., "Aromatic -Stacking in Solution as Revealed through the Aggregation of Phenylacetylene Macrocycles," J. Am. Chem. Soc., 1996, vol. 118, No. 5, pp. 1019-1027.

Somekawa et al., "Intramolecular [2+2]Photocycloadditions of 1-(w-Alkenyl)-2-pyridones Possessing an Ester Group on the Olefinic Carbon Chain," J. Org. Chem., 1992, vol. 57, No. 21, 5708-5712.

Staker et al., "Structures of Three Classes of Anticancer Agents Bound to the Human Topoisomerase I-DNA Covalent Complex," J. Med. Chem., 2005, vol. 48, No. 7, 2336-2345.

Staker et al., "The Mechanism of Topoisomerase I Poisoning by a Camptothecin Analog," Proc. Natl. Acad. Sci. U.S.A., 2002, vol. 99, No. 24, pp. 15387-15392.

Strumberg et al., "Synthesis of Cytotoxic Indenoisoquinoline Topoisomerase I Poisons," J. Med. Chem., 1999, vol. 42, No. 3, pp. 446-457.

Vance et al., "Structural Features of Nitroaromatics That Determine Mutagenic Activity in *Salmonella typhimurium*," Environmental Mutagenesis, 1984, vol. 6, pp. 797-811.

Wang et al., "Differential Effects of Camptothecin Derivatives on Topoisomerase I-Mediated DNA Structure Modification," Biochemistry, 1998, vol. 37, No. 26, 9399-9408.

Wang et al., "Role of the 20-Hydroxyl Group in Camptothecin Binding by the Topoisomerase I-DNA Binary Complex," Biochemistry, 1999, vol. 38, No. 14, 4374-4381.

Wawzonek et al., "The Synthesis and Reactions of 1-Carbamyl-11-ketoindeno[1,2-c]isoquinoline," J. Org. Chem., 1966, vol. 31, pp. 1004-1006.

Whitmore et al., "The Preparation of Homophthalyl Cyclic Hydrazide and 4-Aminohomophthalyl Cyclic Hydrazide," J. Am. Chem. Soc., 1944, vol. 66, pp. 1237-1240.

Xiao et al., "Design, synthesis, and biological evaluation of cytotoxic 11-aminoalkenylindenoisoquinoline and 11-diaminoalkenylindenoisoquinoline topoisomerase I inhibitors," Bioorganic & Medicinal Chemistry, vol. 12 (2004), 5147-5160.

Xiao et al., "Dihydroindenoisoquinolines function as prodrugs of indenoisoquinolines," Bioorganic & Medicinal Chemistry Letters, vol. 15 (2003), 2795-2798.

Xiao et al., "Novel Autoxidative Cleavage Reaction of 9-Fluoredenes Discovered during Synthesis of a Potential DNA-Threading Indenoisoquinoline," J. Org. Chem., 2004, vol. 69, No. 22, 7495-7501.

Xiao et al., "On the Binding of Indeno[1,2-c]isoquinolines in the DNA-Topoisomerase I Cleavage Complex," J. Med. Chem., 2005, vol. 48, No. 9, 3231-3238.

Cho, Won-Jea et al., "A Novel Synthesis of Benzo[c]phenanthridine Skeleton and Biological Evaluation of Isoquinoline Derivatives," Chem. Pharm. Bull. vol. 47, No. 6, 1999, pp. 900-902.

Dyke, S. F. et al., "The Chemistry of Cryptopine-I.", Tetrahedron, vol. 24, No. 3, 1968, pp. 1455-1465.

Fox, Brian M. et al., Design, Synthesis, and Biological Evaluation of Cytotoxic 11-Alkenylindenoisoquinoline Topoisomerase I Inhibitors and Indenoisoquinolone—Camptothecin Hybrids, J. Med. Chem., vol. 46, No. 15, Jul. 2003, pp. 3275-3282.

Shamma, M. et al., "Synthetic Approaches to Camptothecin," Tetrahedron, vol. 25, No. 11, 1969, pp. 2275-2279.

N. Sazonova et al., "Synthesis and antitumor activity of salts of o-methylfagaronine and its analogs C-norbenzo[c]phenanthridine," Chem. Abstracts, vol. 115, No. 17, Oct. 28, 1991, p. 965, col. 1, XP 002415177 Abstract only.

N. Sazonova et al., "Benzophenanthridines. XVI," Chem. Abstracts, vol. 116, No. 17, Apr. 27, 1992, p. 900, col. 1, XP 002415180 Abstract only.

* cited by examiner

1

2

3

4

7

8

CYTOTOXIC INDENO AND ISOINDOLOISOQUINOLONES

CROSS REFERENCE TO RELATED APPLICATIONS

This patent application is a U.S. national counterpart application, filed under 35 U.S.C. § 371(c), of international application Ser. No. PCT/US2004/014581 filed May 11, 2004, which claims the benefit under 35 U.S.C. § 119(e) of U.S. provisional application Ser. No. 60/469,718 filed May 12, 2003, the disclosure of which is incorporated herein by reference.

GOVERNMENT RIGHTS

The government may have rights in this invention. Funding for this disclosure was provided in part by the National Institutes of Health (NIH) Research Grant UO1 CA89566 and Training Grant ST32CA09634, the Developmental Therapeutics Program, DCTD, NCI under Contract NO1-CO-56000, and SBIR grants: NCI SBIR Phase 1 Grant #R43 CA79439-01, Anti-Cancer Drug Design Targeting Human Topoisomerase I; NCI SBIR Phase 2 Grant #R44 CA79439-02, Anti-Cancer Drug Design Targeting Human Topoisomerase I, and NCI SBIR Phase 1 Grant #R43-CA82964-01, Anti-Cancer Compounds Designed to Poison Topoisomerase I.

FIELD OF THE INVENTION

This invention relates to indeno and isoindoloisoquinolones, and uses of indeno and isoindoloisoquinolones as cytotoxic agents.

BACKGROUND OF THE INVENTION

The cytotoxicity profile of the topoisomerase I (top 1) inhibitors camptothecin (3) and indenoisoquinoline 2 (see FIG. 3) has been described by Kohlhagen et al. in *Mol. Pharmacol.* 54:50-58 (1998); Pommier et al. in *Biochem. Biophys. Acta,* 1400:83-105 (1998); and Pommier in *Opinion in Oncologic, Endocrine & Metabolic Investigational Drugs,* 1:168-169 (1999), the disclosures of which are incorporated herein by reference. The synthesis of indenoisoquinoline 2 is accomplished by treatment of the cis-substituted isoquinolone 1 (FIG. 3) with thionyl chloride, as described by Cushman & Cheng in *J. Org. Chem.* 43:3781-83 (1978), the disclosure of which is incorporated herein by reference. Both camptothecin (3) and indenoisoquinoline 2 were also shown to be inhibitors of DNA religation reactions occuring after DNA cleavage by the enzyme, i.e., top1-catalyzed single strand breakage. Both camptothecin (3) and indenoisoquinoline 2 might be better classified as a top1 poisons than a top1 suppressors because camptothecin (3) and indenoisoquinoline 2 showed the ability to stabilize the cleavable complexes. However, the DNA single-strand breaks induced by indenoisoquinoline 2 were more stable than those induced by camptothecin (3). Furthermore, the cleavage site specificity of 2 was different from that of camptothecin (3).

Although several camptothecin (3) derivatives such as irinotecan and topotecan are clinically useful anticancer agents, they are unstable due to opening of the lactone ring present on each of these compounds; thus, subsequent rapid reversibility of the cleavage complexes is observed after drug removal. Consequently, there is a present need for additional therapeutic agents that inhibit top1 like the camptothecins, but that induce novel DNA cleavage patterns, have modified toxicity profiles and extended durations of action, and display different antitumor spectra relative to the camptothecins themselves. A number of analogs of the indenoisoquinoline 2 have been synthesized, as described by Strumberg et al. in *J. Med. Chem.* 42:446-457 (1999); Cushman et al. in *J. Med. Chem.* 43:3688-3698 (2000); and Jayaraman et al. in *J. Med. Chem.* 45:242-249 (2002).

SUMMARY OF THE INVENTION

A compound of formula I is described:

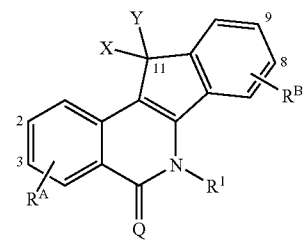

wherein

Q is oxygen or sulfur;

X is hydrogen and Y is $CHR^2R^3$, $NHR^2$, $NHOR^2$, or $NHNR^2R^3$; or X and Y are taken together to form $=CR^2R^3$; $=NR^2$; $=NOR^2$; or $=NNR^2R^3$;

$R^1$, $R^2$, and $R^3$ are each independently selected from the group consisting of hydrogen and a radical $-(CH_2)_mZ$, where m is an integer from 0-6 and Z is selected from the group consisting of halogen, hydroxy, formyl, $C_1$-$C_6$ alkanoyloxy, optionally substituted benzoyloxy, $C_1$-$C_6$ alkyl, $C_1$-$C_6$ alkoxy, $C_3$-$C_8$ cycloalkyl, $C_3$-$C_8$ cycloalkoxy, $C_2$-$C_6$ alkenyl, $C_2$-$C_6$ alkynyl, $C_1$-$C_6$ haloalkyl, $C_1$-$C_6$ haloalkoxy, $C_3$-$C_8$ halocycloalkyl, $C_3$-$C_8$ halocycloalkoxy, amino, $C_1$-$C_6$ alkylamino, ($C_1$-$C_6$ alkyl)($C_1$-$C_6$ alkyl)amino, alkylcarbonylamino, N—($C_1$-$C_6$ alkyl)alkylcarbonylamino, aminoalkyl, $C_1$-$C_6$ alkylaminoalkyl, ($C_1$-$C_6$ alkyl)($C_1$-$C_6$ alkyl)aminoalkyl, alkylcarbonylaminoalkyl, N—($C_1$-$C_6$ alkyl)alkylcarbonylaminoalkyl, cyano, nitro, $C_1$-$C_6$ alkylsulfonyl, optionally substituted phenyl, optionally substituted phenoxy, and optionally substituted heteroaryl; or Z is selected from the group consisting of $—N_3$, $—CO_2R^4$, $—CONR^5R^6$, $—P(O)(OR^4)_2$, $—P(O)(NR^4R^5)_2$, and $—P(O)(NR^4R^5)(OR^4)$, where $R^4$, $R^5$, and $R^6$ are each independently selected in each occurrence from the group consisting of hydrogen, $C_1$-$C_6$ alkyl, $C_3$-$C_8$ cycloalkyl, $C_1$-$C_6$ haloalkyl, optionally substituted phenyl, and optionally substituted phenyl-$C_1$-$C_6$ alkyl; or when X and Y are taken together to form $=NNR^2R^3$, $R^2$ and $R^3$ are taken together with the attached nitrogen to form an optionally substituted heterocycle;

$R^A$ represents 1-4 substituents each independently selected from the group consisting of hydrogen and a radical $—(CH_2)_{m'}Z'$, where m' is an integer from 0-6 and Z' is selected from the group consisting of halogen, hydroxy, $C_1$-$C_6$ alkanoyloxy, optionally substituted benzoyloxy, $C_1$-$C_6$ alkyl, $C_1$-$C_6$ alkoxy, $C_3$-$C_8$ cycloalkyl, $C_3$-$C_8$ cycloalkoxy, $C_2$-$C_6$ alkenyl, $C_2$-$C_6$ alkynyl, $C_1$-$C_6$ haloalkyl, $C_1$-$C_6$ haloalkoxy, $C_3$-$C_8$ halocycloalkyl, $C_3$-$C_8$ halocycloalkoxy, amino, $C_1$-$C_6$ alkylamino, ($C_1$-$C_6$ alkyl)($C_1$-$C_6$ alkyl)amino, alkylcarbonylamino, N—($C_1$-$C_6$ alkyl)alkylcarbonylamino, aminoalkyl, $C_1$-$C_6$ alkylaminoalkyl, ($C_1$-$C_6$ alkyl)($C_1$-$C_6$ alkyl)aminoalkyl, alkylcarbonylaminoalkyl, N—($C_1$-$C_6$ alkyl)alkylcarbonylaminoalkyl, cyano, nitro, $C_1$-$C_6$ alkylsulfonyl, optionally substituted phenyl, optionally substituted phenoxy, and optionally substituted heteroaryl; or Z' is selected from the group consisting of —$N_3$, —$CO_2R^{4'}$, —$CONR^{5'}R^{6'}$, —$P(O)(OR^{4'})_2$, —$P(O)(NR^{4'}R^{5'})_2$, and —$P(O)(NR^{4'}R^{5'})(OR^{4'})$, where $R^{4'}$, $R^{5'}$, and $R^{6'}$ are each independently selected in each occurrence from the group consisting of hydrogen, $C_1$-$C_6$ alkyl, $C_3$-$C_8$ cycloalkyl, $C_1$-$C_6$ haloalkyl, optionally substituted phenyl, and optionally substituted phenyl-$C_1$-$C_6$ alkyl; or $R^A$ represents 2-4 substituents where 2 of said substituents are adjacent substituents and are taken together with the attached carbons to form an optionally substituted carbocycle or an optionally substituted heterocycle, and the remaining 2 substituents are each independently selected from the group consisting of hydrogen and a radical —$(CH_2)_{m'}Z'$, where m' is an integer from 0-6 and Z' is selected from the group consisting of halogen, hydroxy, $C_1$-$C_6$ alkanoyloxy, optionally substituted benzoyloxy, $C_1$-$C_6$ alkyl, $C_1$-$C_6$ alkoxy, $C_3$-$C_8$ cycloalkyl, $C_3$-$C_8$ cycloalkoxy, $C_2$-$C_6$ alkenyl, $C_2$-$C_6$ alkynyl, $C_1$-$C_6$ haloalkyl, $C_1$-$C_6$ haloalkoxy, $C_3$-$C_8$ halocycloalkyl, $C_3$-$C_8$ halocycloalkoxy, amino, $C_1$-$C_6$ alkylamino, ($C_1$-$C_6$ alkyl)($C_1$-$C_6$ alkyl)amino, alkylcarbonylamino, N—($C_1$-$C_6$ alkyl)alkylcarbonylamino, aminoalkyl, $C_1$-$C_6$ alkylaminoalkyl, ($C_1$-$C_6$ alkyl)($C_1$-$C_6$ alkyl)aminoalkyl, alkylcarbonylaminoalkyl, N—($C_1$-$C_6$ alkyl)alkylcarbonylaminoalkyl, cyano, nitro, $C_1$-$C_6$ alkylsulfonyl, optionally substituted phenyl, optionally substituted phenoxy, and optionally substituted heteroaryl; or Z' is selected from the group consisting of —$N_3$, —$CO_2R^{4'}$, —$CONR^{5'}R^{6'}$, —$P(O)(OR^{4'})_2$, —$P(O)(NR^{4'}R^{5'})_2$, and —$P(O)(NR^{4'}R^{5'})(OR^{4'})$, where $R^{4'}$, $R^{5'}$, and $R^{6'}$ are each independently selected in each occurrence from the group consisting of hydrogen, $C_1$-$C_6$ alkyl, $C_3$-$C_8$ cycloalkyl, $C_1$-$C_6$ haloalkyl, optionally substituted phenyl, and optionally substituted phenyl-$C_1$-$C_6$ alkyl; and $R^B$ represents 1-4 substituents each independently selected from the group consisting of hydrogen and a radical —$(CH_2)_{m''}Z''$, where m'' is an integer from 0-6 and Z'' is selected from the group consisting of halogen, hydroxy, $C_1$-$C_6$ alkanoyloxy, optionally substituted benzoyloxy, $C_1$-$C_6$ alkyl, $C_1$-$C_6$ alkoxy, $C_3$-$C_8$ cycloalkyl, $C_3$-$C_8$ cycloalkoxy, $C_2$-$C_6$ alkenyl, $C_2$-$C_6$ alkynyl, $C_1$-$C_6$ haloalkyl, $C_1$-$C_6$ haloalkoxy, $C_3$-$C_8$ halocycloalkyl, $C_3$-$C_8$ halocycloalkoxy, amino, $C_1$-$C_6$ alkylamino, ($C_1$-$C_6$ alkyl)($C_1$-$C_6$ alkyl)amino, alkylcarbonylamino, N—($C_1$-$C_6$ alkyl)alkylcarbonylamino, aminoalkyl, $C_1$-$C_6$ alkylaminoalkyl, ($C_1$-$C_6$ alkyl)($C_1$-$C_6$ alkyl)aminoalkyl, alkylcarbonylaminoalkyl, N—($C_1$-$C_6$ alkyl)alkylcarbonylaminoalkyl, cyano, nitro, $C_1$-$C_6$ alkylsulfonyl, optionally substituted phenyl, optionally substituted phenoxy, and optionally substituted heteroaryl; or Z'' is selected from the group consisting of —$N_3$, —$CO_2R^{4''}$, —$CONR^{5''}R^{6''}$, —$P(O)(OR^{4''})_2$, —$P(O)(NR^{4''}R^{5''})_2$, and —$P(O)(NR^{4''}R^{5''})(OR^{4''})$, where $R^{4''}$, $R^{5''}$, and $R^{6''}$ are each independently selected in each occurrence from the group consisting of hydrogen, $C_1$-$C_6$ alkyl, $C_3$-$C_8$ cycloalkyl, $C_1$-$C_6$ haloalkyl, optionally substituted phenyl, and optionally substituted phenyl-$C_1$-$C_6$ alkyl; or $R^B$ represents 2-4 substituents where 2 of said substituents are adjacent substituents and are taken together with the attached carbons to form an optionally substituted carbocycle or an optionally substituted heterocycle, and the remaining 2 substituents are each independently selected from the group consisting of hydrogen and a radical —$(CH_2)_{m''}Z''$, where m'' is an integer from 0-6 and Z'' is selected from the group consisting of halogen, hydroxy, $C_1$-$C_6$ alkanoyloxy, optionally substituted benzoyloxy, $C_1$-$C_6$ alkyl, $C_1$-$C_6$ alkoxy, $C_3$-$C_8$ cycloalkyl, $C_3$-$C_8$ cycloalkoxy, $C_2$-$C_6$ alkenyl, $C_2$-$C_6$ alkynyl, $C_1$-$C_6$ haloalkyl, $C_1$-$C_6$ haloalkoxy, $C_3$-$C_8$ halocycloalkyl, $C_3$-$C_8$ halocycloalkoxy, amino, $C_1$-$C_6$ alkylamino, ($C_1$-$C_6$ alkyl)($C_1$-$C_6$ alkyl)amino, alkylcarbonylamino, N—($C_1$-$C_6$ alkyl)alkylcarbonylamino, aminoalkyl, $C_1$-$C_6$ alkylaminoalkyl, ($C_1$-$C_6$ alkyl)($C_1$-$C_6$ alkyl)aminoalkyl, alkylcarbonylaminoalkyl, N—($C_1$-$C_6$ alkyl)alkylcarbonylaminoalkyl, cyano, nitro, $C_1$-$C_6$ alkylsulfonyl, optionally substituted phenyl, optionally substituted phenoxy, and optionally substituted heteroaryl; or Z'' is selected from the group consisting of —$N_3$, —$CO_2R^{4''}$, —$CONR^{5''}R^{6''}$, —$P(O)(OR^{4''})_2$, —$P(O)(NR^{4''}R^{5''})_2$, and —$P(O)(NR^{4''}R^{5''})(OR^{4''})$, where $R^{4''}$, $R^{5''}$, and $R^{6''}$ are each independently selected in each occurrence from the group consisting of hydrogen, $C_1$-$C_6$ alkyl, $C_3$-$C_8$ cycloalkyl, $C_1$-$C_6$ haloalkyl, optionally substituted phenyl, and optionally substituted phenyl-$C_1$-$C_6$ alkyl is described.

In one illustrative embodiment of the compounds of formula I, Q is oxygen; and $R^A$ is 2,3-bis($C_1$-$C_6$ alkoxy). In another illustrative embodiment of the compounds of formula I, Q is oxygen; and $R^1$ is $C_1$-$C_6$ alkyl, aminoalkyl, or $C_1$-$C_6$ haloalkyl. In one illustrative embodiment of the compounds of formula I, $R^B$ represents 2-4 substituents where 2 of the substituents are adjacent substituents and are taken together with the attached carbons to form an heterocycle selected from dioxolane and dioxane.

In another illustrative embodiment of the compounds of formula I, Q is oxygen, $R^A$ is 2,3-bis($C_1$-$C_6$ alkoxy), $R^B$ is 8,9-alkylenedioxy, X and Y are taken together to form =$CR^2R^3$, where $R^2$ is hydrogen and $R^3$ is as described above, and $R^1$ is as described above. In another illustrative embodiment of the compounds of formula I, Q is oxygen, $R^A$ is 2,3-bis($C_1$-$C_6$ alkoxy), $R^B$ is 8,9-alkylenedioxy, X and Y are taken together to form =$CR^2R^3$, where $R^2$ is hydrogen and $R^3$ is as described above, and $R^1$ is hydrogen, $C_1$-$C_6$ alkyl, $C_3$-$C_8$ cycloalkyl, $C_1$-$C_6$ haloalkyl, $C_3$-$C_8$ halocycloalkyl, amino-$C_1$-$C_6$ alkyl, $C_1$-$C_6$ alkylamino-$C_1$-$C_6$ alkyl, or ($C_1$-$C_6$ alkyl)($C_1$-$C_6$ alkyl)amino-$C_1$-$C_6$ alkyl.

In another illustrative embodiment of the compounds of formula I, X and Y are taken together to form =$CR^2R^3$, where $R^2$ and $R^3$ are as described above. In one aspect, the carbon-carbon double bond formed thereby is an E-double bond. In another aspect, the carbon-carbon double bond formed thereby is an Z-double bond. In another illustrative embodiment of the compounds of formula I, X and Y are taken together to form =$CR^2R^3$; and $R^2$ is $C_1$-$C_6$ haloalkyl or aminoalkyl. In one aspect, $R^1$ is hydrogen.

In another illustrative embodiment of the compounds of formula I, Z is selected from hydroxy, amino, $C_1$-$C_6$ alkylamino, and nitro. In another illustrative embodiment of the compounds of formula I, Z' is selected from $C_1$-$C_6$ alkoxy and nitro. In another illustrative embodiment of the compounds of formula I, Z'' is selected from $C_1$-$C_6$ alkoxy and nitro.

In another illustrative embodiment of the compounds of formula I, $R^B$ represents 2-4 substituents where 2 of substituents are adjacent substituents and are taken together with the attached carbons to form an optionally substituted heterocycle. In another illustrative embodiment of the compounds of formula I, $R^B$ represents 2-4 substituents where 2 of said substituents are adjacent substituents and are taken together with the attached carbons to form an optionally substituted heterocycle; and Z'' is selected from $C_1$-$C_6$ alkoxy and nitro.

A compound of formula II is described:

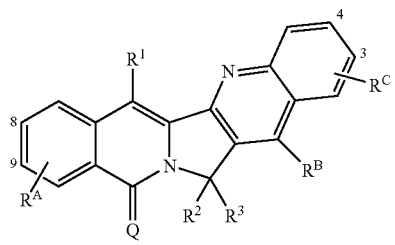

wherein

Q is oxygen or sulfur;

R₁, R², and R³ are each independently selected from the group consisting of hydrogen and a radical —(CH$_2$)$_m$Z, where m is an integer from 0-6 and Z is selected from the group consisting of halogen, hydroxy, formyl, $C_1$-$C_6$ alkanoyloxy, optionally substituted benzoyloxy, $C_1$-$C_6$ alkyl, $C_1$-$C_6$ alkoxy, $C_3$-$C_8$ cycloalkyl, $C_3$-$C_8$ cycloalkoxy, $C_2$-$C_6$ alkenyl, $C_2$-$C_6$ alkynyl, $C_1$-$C_6$ haloalkyl, $C_1$-$C_6$ haloalkoxy, $C_3$-$C_8$ halocycloalkyl, $C_3$-$C_8$ halocycloalkoxy, amino, $C_1$-$C_6$ alkylamino, ($C_1$-$C_6$ alkyl)($C_1$-$C_6$ alkyl)amino, alkylcarbonylamino, N—($C_1$-$C_6$ alkyl)alkylcarbonylamino, aminoalkyl, $C_1$-$C_6$ alkylaminoalkyl, ($C_1$-$C_6$ alkyl)($C_1$-$C_6$ alkyl)aminoalkyl, alkylcarbonylaminoalkyl, N—($C_1$-$C_6$ alkyl)alkylcarbonylaminoalkyl, cyano, nitro, $C_1$-$C_6$ alkylsulfonyl, optionally substituted phenyl, optionally substituted phenoxy, and optionally substituted heteroaryl; or Z is selected from the group consisting of —N$_3$, —CO$_2$R⁴, —CONR⁵R⁶, —P(O)(OR⁴)$_2$, —P(O)(NR⁴R⁵)$_2$, and —P(O)(NR⁴R⁵)(OR⁴), where R⁴, R⁵, and R⁶ are each independently selected in each occurrence from the group consisting of hydrogen, $C_1$-$C_6$ alkyl, $C_3$-$C_8$ cycloalkyl, $C_1$-$C_6$ haloalkyl, optionally substituted phenyl, and optionally substituted phenyl-$C_1$-$C_6$ alkyl; or R¹ is selected from the group consisting of hydrogen and a radical —(CH$_2$)$_m$Z, where m is an integer from 0-6 and Z is selected from the group consisting of halogen, hydroxy, formyl, $C_1$-$C_6$ alkanoyloxy, optionally substituted benzoyloxy, $C_1$-$C_6$ alkyl, $C_1$-$C_6$ alkoxy, $C_3$-$C_8$ cycloalkyl, $C_3$-$C_8$ cycloalkoxy, $C_2$-$C_6$ alkenyl, $C_2$-$C_6$ alkynyl, $C_1$-$C_6$ haloalkyl, $C_1$-$C_6$ haloalkoxy, $C_3$-$C_8$ halocycloalkyl, $C_3$-$C_8$ halocycloalkoxy, amino, $C_1$-$C_6$ alkylamino, ($C_1$-$C_6$ alkyl)($C_1$-$C_6$ alkyl)amino, alkylcarbonylamino, N—($C_1$-$C_6$ alkyl)alkylcarbonylamino, aminoalkyl, $C_1$-$C_6$ alkylaminoalkyl, ($C_1$-$C_6$ alkyl)($C_1$-$C_6$ alkyl)aminoalkyl, alkylcarbonylaminoalkyl, N—($C_1$-$C_6$ alkyl)alkylcarbonylaminoalkyl, cyano, nitro, $C_1$-$C_6$ alkylsulfonyl, optionally substituted phenyl, optionally substituted phenoxy, and optionally substituted heteroaryl; or Z is selected from the group consisting of —N$_3$, —CO$_2$R⁴, —CONR⁵R⁶, —P(O)(OR⁴)$_2$, —P(O)(NR⁴R⁵)$_2$, and —P(O)(NR⁴R⁵)(OR⁴), where R⁴, R⁵, and R⁶ are each independently selected from the group consisting of hydrogen, $C_1$-$C_6$ alkyl, $C_3$-$C_8$ cycloalkyl, $C_1$-$C_6$ haloalkyl, optionally substituted phenyl, and optionally substituted phenyl-$C_1$-$C_6$ alkyl; and R² and R³ are taken together with the attached carbon to form an optionally substituted carbocycle or heterocycle;

R$^A$ represents 1-4 substituents each independently selected from the group consisting of hydrogen and a radical —(CH$_2$)$_{m'}$Z', where m' is an integer from 0-6 and Z' is selected from the group consisting of halogen, hydroxy, $C_1$-$C_6$ alkanoyloxy, optionally substituted benzoyloxy, $C_1$-$C_6$ alkyl, $C_1$-$C_6$ alkoxy, $C_3$-$C_8$ cycloalkyl, $C_3$-$C_8$ cycloalkoxy, $C_2$-$C_6$ alkenyl, $C_2$-$C_6$ alkynyl, $C_1$-$C_6$ haloalkyl, $C_1$-$C_6$ haloalkoxy, $C_3$-$C_8$ halocycloalkyl, $C_3$-$C_8$ halocycloalkoxy, amino, $C_1$-$C_6$ alkylamino, ($C_1$-$C_6$ alkyl)($C_1$-$C_6$ alkyl)amino, alkylcarbonylamino, N—($C_1$-$C_6$ alkyl)alkylcarbonylamino, aminoalkyl, $C_1$-$C_6$ alkylaminoalkyl, ($C_1$-$C_6$ alkyl)($C_1$-$C_6$ alkyl)aminoalkyl, alkylcarbonylaminoalkyl, N—($C_1$-$C_6$ alkyl)alkylcarbonylaminoalkyl, cyano, nitro, $C_1$-$C_6$ alkylsulfonyl, optionally substituted phenyl, optionally substituted phenoxy, and optionally substituted heteroaryl; or Z' is selected from the group consisting of —N$_3$, —CO$_2$R⁴', —CONR⁵'R⁶', —P(O)(OR⁴')$_2$, —P(O)(NR⁴'R⁵')$_2$, and —P(O)(NR⁴'R⁵')(OR⁴'), where R⁴', R⁵', and R⁶' are each independently selected in each occurrence from the group consisting of hydrogen, $C_1$-$C_6$ alkyl, $C_3$-$C_8$ cycloalkyl, $C_1$-$C_6$ haloalkyl, optionally substituted phenyl, and optionally substituted phenyl-$C_1$-$C_6$ alkyl; or R$^A$ represents 2-4 substituents where 2 of said substituents are adjacent substituents and are taken together with the attached carbons to form an optionally substituted carbocycle or an optionally substituted heterocycle, and the remaining 2 substituents are each independently selected from the group consisting of hydrogen and a radical —(CH$_2$)$_{m'}$Z', where m' is an integer from 0-6 and Z' is selected from the group consisting of halogen, hydroxy, $C_1$-$C_6$ alkanoyloxy, optionally substituted benzoyloxy, $C_1$-$C_6$ alkyl, $C_1$-$C_6$ alkoxy, $C_3$-$C_8$ cycloalkyl, $C_3$-$C_8$ cycloalkoxy, $C_2$-$C_6$ alkenyl, $C_2$-$C_6$ alkynyl, $C_1$-$C_6$ haloalkyl, $C_1$-$C_6$ haloalkoxy, $C_3$-$C_8$ halocycloalkyl, $C_3$-$C_8$ halocycloalkoxy, amino, $C_1$-$C_6$ alkylamino, ($C_1$-$C_6$ alkyl)($C_1$-$C_6$ alkyl)amino, alkylcarbonylamino, N—($C_1$-$C_6$ alkyl)alkylcarbonylamino, aminoalkyl, $C_1$-$C_6$ alkylaminoalkyl, ($C_1$-$C_6$ alkyl)($C_1$-$C_6$ alkyl)aminoalkyl, alkylcarbonylaminoalkyl, N—($C_1$-$C_6$ alkyl)alkylcarbonylaminoalkyl, cyano, nitro, $C_1$-$C_6$ alkylsulfonyl, optionally substituted phenyl, optionally substituted phenoxy, and optionally substituted heteroaryl; or Z' is selected from the group consisting of —N$_3$, —CO$_2$R⁴', —CONR⁵'R⁶', —P(O)(OR⁴')$_2$, —P(O)NR⁴'R⁵')$_2$ and —P(O)(NR⁴'R⁵')(OR⁴'), where R⁴', R⁵', and R⁶' are each independently selected in each occurrence from the group consisting of hydrogen, $C_1$-$C_6$ alkyl, $C_3$-$C_8$ cycloalkyl, $C_1$-$C_6$ haloalkyl, optionally substituted phenyl, and optionally substituted phenyl-$C_1$-$C_6$ alkyl;

R$^B$ is selected from the group consisting of hydrogen and a radical —(CH$_2$)$_{m''}$Z'', where m'' is an integer from 0-6 and Z'' is selected from the group consisting of halogen, hydroxy, $C_1$-$C_6$ alkanoyloxy, optionally substituted benzoyloxy, $C_1$-$C_6$ alkyl, $C_1$-$C_6$ alkoxy, $C_3$-$C_8$ cycloalkyl, $C_3$-$C_8$ cycloalkoxy, $C_2$-$C_6$ alkenyl, $C_2$-$C_6$ alkynyl, $C_1$-$C_6$ haloalkyl, $C_1$-$C_6$ haloalkoxy, $C_3$-$C_8$ halocycloalkyl, $C_3$-$C_8$ halocycloalkoxy, amino, $C_1$-$C_6$ alkylamino, ($C_1$-$C_6$ alkyl)($C_1$-$C_6$ alkyl)amino, alkylcarbonylamino, N—($C_1$-$C_6$ alkyl)alkylcarbonylamino, aminoalkyl, $C_1$-$C_6$ alkylaminoalkyl, ($C_1$-$C_6$ alkyl)($C_1$-$C_6$ alkyl)aminoalkyl, alkylcarbonylaminoalkyl, N—($C_1$-$C_6$ alkyl)alkylcarbonylaminoalkyl, cyano, nitro, $C_1$-$C_6$ alkylsulfonyl, optionally substituted phenyl, optionally substituted phenoxy, and optionally substituted heteroaryl; or Z'' is selected from the group consisting of —N$_3$, —CO$_2$R⁴'', —CONR⁵''R⁶'', —P(O)(OR⁴'')$_2$, —P(O)(NR⁴''R⁵'')$_2$, and —P(O)(NR⁴''R⁵'')(OR⁴''), where R⁴'', R⁵'', and R⁶'' are each independently selected in each occurrence from the group consisting of hydrogen, $C_1$-$C_6$ alkyl, $C_3$-$C_8$ cycloalkyl, $C_1$-$C_6$ haloalkyl, optionally substituted phenyl, and optionally substituted phenyl-$C_1$-$C_6$ alkyl; and R$^C$ represents 1-4 substituents each independently selected from the group consisting of hydrogen and a radical —(CH$_2$)$_{m'''}$Z''', where m''' is an integer from 0-6 and Z''' is selected from the group consisting of halogen, hydroxy, $C_1$-$C_6$ alkanoyloxy, optionally substituted benzoyloxy, $C_1$-$C_6$ alkyl, $C_1$-$C_6$ alkoxy, $C_3$-$C_8$ cycloalkyl, $C_3$-$C_8$ cycloalkoxy, $C_2$-$C_6$ alkenyl, $C_2$-$C_6$ alkynyl, $C_1$-$C_6$ haloalkyl, $C_1$-$C_6$ haloalkoxy, $C_3$-$C_8$ halocycloalkyl, $C_3$-$C_8$ halocycloalkoxy, amino, $C_1$-$C_6$ alkylamino, ($C_1$-$C_6$ alkyl)($C_1$-$C_6$ alkyl)amino, alkylcarbonylamino, N—($C_1$-$C_6$ alkyl)alkylcarbonylamino, aminoalkyl, $C_1$-$C_6$ alkylaminoalkyl, ($C_1$-$C_6$ alkyl)($C_1$-$C_6$ alkyl)aminoalkyl, alkylcarbonylaminoalkyl, N—($C_1$-$C_6$ alkyl)alkylcarbonylaminoalkyl, cyano, nitro, $C_1$-$C_6$ alkylsulfonyl, optionally substituted phenyl, optionally substituted phenoxy, and optionally substituted heteroaryl; or Z''' is selected from the group consisting of —$N_3$, —$CO_2R^{4'''}$, —$CONR^{5'''}R^{6'''}$, —$P(O)(OR^{4'''})_2$, —$P(O)(NR^{4'''}R^{5'''})_2$, and —$P(O)(NR^{4'''}R^{5'''})(OR^{4'''})$, where $R^{4'''}$, $R^{5'''}$, and $R^{6'''}$ are each independently selected in each occurrence from the group consisting of hydrogen, $C_1$-$C_6$ alkyl, $C_3$-$C_8$ cycloalkyl, $C_1$-$C_6$ haloalkyl, optionally substituted-phenyl, and optionally substituted phenyl-$C_1$-$C_6$ alkyl; or $R^C$ represents 2-4 substituents where 2 of said substituents are adjacent substituents and are taken together with the attached carbons to form an optionally substituted carbocycle or an optionally substituted heterocycle, and the remaining 2 substituents are each independently selected from the group consisting of hydrogen and a radical —$(CH_2)_{m'''}Z'''$, where m''' is an integer from 0-6 and Z''' is selected from the group consisting of halogen, hydroxy, $C_1$-$C_6$ alkanoyloxy, optionally substituted benzoyloxy, $C_1$-$C_6$ alkyl, $C_1$-$C_6$ alkoxy, $C_3$-$C_8$ cycloalkyl, $C_3$-$C_8$ cycloalkoxy, $C_2$-$C_6$ alkenyl, $C_2$-$C_6$ alkynyl, $C_1$-$C_6$ haloalkyl, $C_1$-$C_6$ haloalkoxy, $C_3$-$C_8$ halocycloalkyl, $C_3$-$C_8$ halocycloalkoxy, amino, $C_1$-$C_6$ alkylamino, ($C_1$-$C_6$ alkyl)($C_1$-$C_6$ alkyl)amino, alkylcarbonylamino, N—($C_1$-$C_6$ alkyl)alkylcarbonylamino, aminoalkyl, $C_1$-$C_6$ alkylaminoalkyl, ($C_1$-$C_6$ alkyl)($C_1$-$C_6$ alkyl)aminoalkyl, alkylcarbonylaminoalkyl, N—($C_1$-$C_6$ alkyl)alkylcarbonylaminoalkyl, cyano, nitro, $C_1$-$C_6$ alkylsulfonyl, optionally substituted phenyl, optionally substituted phenoxy, and optionally substituted heteroaryl; or Z''' is selected from the group consisting of —$N_3$, —$CO_2R^{4'''}$, —$CONR^{5'''}R^{6'''}$, —$P(O)(OR^{4'''})_2$, $P(O)(NR^{4'''}R^{5'''})_2$, and —$P(O)(NR^{4'''}R^{5'''})(OR^{4'''})$, where $R^{4'''}$, $R^{5'''}$, and $R^{6'''}$ are each independently selected in each occurrence from the group consisting of hydrogen, $C_1$-$C_6$ alkyl, $C_3$-$C_8$ cycloalkyl, $C_1$-$C_6$ haloalkyl, optionally substituted phenyl, and optionally substituted phenyl-$C_1$-$C_6$ alkyl is described.

In one illustrative embodiment of the compounds of formula II, at least one of $R^1$, $R^2$, $R^3$, $R^4$, $R^B$, or $R^C$ is not hydrogen. In another illustrative embodiment of the compounds of formula II, $R^4$ is 2,3-bis($C_1$-$C_6$ alkoxy). In another illustrative embodiment of the compounds of formula II, Q is oxygen, $R^4$ is 2,3-bis($C_1$-$C_6$ alkoxy), and $R^B$, $R^C$, $R^1$, $R^2$, and $R^3$ are each hydrogen.

In another illustrative embodiment of the compounds of formula II, Z' is selected from the group consisting of hydroxy and nitro. In another illustrative embodiment of the compounds of formula II, $R^4$ represents 2-4 substituents where 2 of said substituents are adjacent substituents and are taken together with the attached carbons to form an optionally substituted carbocycle or an optionally substituted heterocycle, and the remaining 2 substituents are each independently selected from the group consisting of hydrogen and a radical —$(CH_2)_m Z'$, where Z' is selected from the group consisting of hydroxy and nitro.

In another illustrative embodiment of the compounds of formula II, wherein Z'' is nitro. In another illustrative embodiment of the compounds of formula II, Z''' is nitro. In another illustrative embodiment of the compounds of formula II, $R^C$ represents 2-4 substituents where 2 of said substituents are adjacent substituents and are taken together with the attached carbons to form an optionally substituted carbocycle or an optionally substituted heterocycle, and the remaining 2 substituents are each independently selected from the group consisting of hydrogen and a radical —$(CH_2)_{m''}Z''$; and Z''' is nitro.

A pharmaceutical composition including one or more compounds of formula I and/or one or more compounds of formula II, and one or more pharmaceutically acceptable carriers, excipients, and/or diluents therefor is also described.

A method for treating a mammal in need of relief from a disease state, including but not limited to cancer, is also described. The method comprises the step of administering to the mammal an effective amount of one or more compounds of formula I and/or one or more compounds of formula II; or an effective amount of a pharmaceutical composition including one or more compounds of formula I and/or one or more compounds of formula II.

DETAILED DESCRIPTION OF THE INVENTION

In one embodiment, indenoisoquinolones of formula I are described herein:

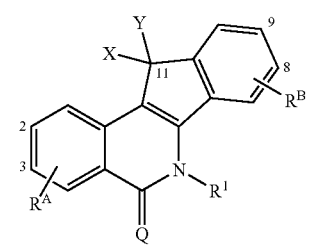

wherein $R^1$, $R^4$, $R^B$, Q, X, and Y are as defined above.

In an embodiment of the compounds of formula I, haloalkyl, aminoalkyl, haloalkenyl, and/or aminoalkenyl side chains may be attached to C-11, as described herein. Halo refers to fluoro, chloro, bromo, and iodo. In another embodiment of the compounds of formula I, heteroaryl alkyl and/or heteroaryl alkenyl side chains may be attached to C-11, as described herein. Heteroaryl refers to any cyclic aromatic structure comprising carbon and including at least one heteroatom, such as nitrogen, oxygen, phosphorus, or sulfur. Illustrative heteroaryls include, but are not limited to, furanyl, thiofuranyl, pyrrolyl, pyrazolyl, imidazolyl, triazolyl, tetrazolyl, oxazolyl, isoxazolyl, thiazolyl, isothiazolyl, oxathiazolyl, pyridinyl, pyridazinyl, pyrimidinyl, pyrazinyl, triazinyl, and the like.

It is appreciated that when X and Y are taken together to form =CR$^2$R$^3$; =NR$^2$; =NOR$^2$; or =NNR$^2$R$^3$, either the E double bond, the Z double bond, or any mixture of E and Z double bond isomers may be formed depending upon the reaction conditions chosen. For example, double bond formation using the McMurry coupling may tend to form more of, substantially more of, or exclusively the E double bond isomer. Other double bond forming reactions, such Wittig olefinations, Peterson olefinations, condensation reactions, dehydration reactions, and the like, may preferentially form other double bond isomers or mixtures thereof.

In another embodiment, isoindoloisoquinolone compounds are described herein. In one aspect, benzo-fused isoindoloisoquinolone compounds are described herein. In another aspect, isoindoloisoquinolone compounds of formula II are described herein:

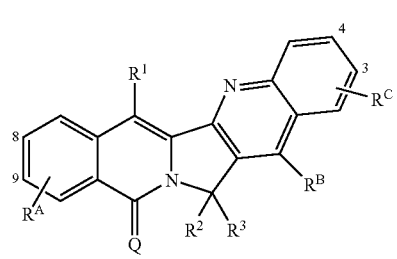

II wherein R$^1$, R$^2$, R$^3$, R$^4$, R$^B$, R$^C$, and Q are as defined above.

Figure 4:
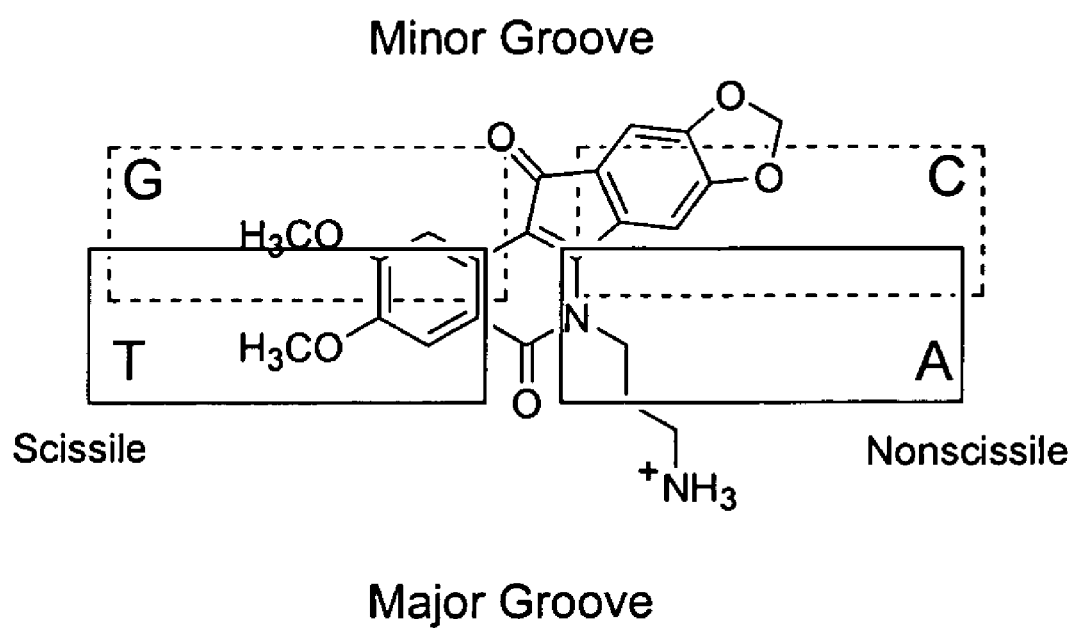
FIG. 4 shows an illustrative model of the orientation of compound 7 relative to DNA in a ternary complex containing top1, DNA, and compound 7.

It is appreciated that compounds of formulae I and II may derive their activity in modifying the growth or proliferation cells, such as cancer cells, from their ability to intercalate into DNA. In particular, DNA unwinding studies indicated that N-3-aminoalkyl derivatives of indenoisoquinolines, such as compound 7, can intercalate. Without being bound by theory, it is suggested that the cationic side chain on the indenoisoquinoline nitrogen of compound 7 may project into the major groove of DNA, as shown in FIG. 4. When the DNA is in a complex with a protein such as top1, side chains on the indenoisoquinoline nitrogen of compounds such as compound 7 may project into the major groove of DNA towards the Asn352 residue of the protein. Regarding compounds of formula I and without being bound by theory, it is suggested that side chains attached at C-11, such as alkyl, alkylidenyl, aminoalkyl, aminoalkylidenyl, hydroxylaminoalkyl, hydroxylaminoalkylidenyl, hydrazinoalkyl, and hydrazinoalkylidenyl side chains, may project into the minor groove of DNA. When the DNA is in a complex with a protein such as top 1, side chains may project into the minor groove of DNA toward the Arg364 and Asp533 residues of the enzyme.

In another embodiment, pharmaceutical compositions and formulations are contemplated herein. Such pharmaceutical compositions and formulations comprise an effective amount of one or more indenoisoquinolone or isoindoloisoquinolone compounds of formulae I and II for treating a patient having cancer. As used herein, an effective amount of the indenoisoquinolone or isoindoloisoquinolone compound is defined as the amount of the compound which, upon administration to a patient, inhibits growth of cancer cells, kills malignant cells, reduces the volume or size of the tumors, or eliminates the tumor entirely in the treated patient.

The effective amount to be administered to a patient is typically based on body surface area, patient weight, and/or patient condition. The interrelationship of dosages for animals and humans (based on milligrams per meter squared of body surface) is described by Freireich, E. J., et al., Cancer Chemother. Rep. 1966, 50 (4), 219. Body surface area may be approximately determined from patient height and weight (see e.g., Scientific Tables, Geigy Pharmaceuticals, Ardley, N.Y., pages 537-538 (1970)). An effective amount of the indenoisoquinolone or isoindoloisoquinolne compounds described herein includes any amount useful for inhibiting the growth of (or killing) cancer cells in a patient. Typically, such effective amounts range from about 5 mg/kg to about 500 mg/kg, more preferably from about 5 mg/kg to about 250 mg/kg, and most preferably about 5 to about 150 mg/kg. It is appreciated that effective doses may also vary dependent on a selected route of administration, excipient usage, and/or the possibility of co-usage with other therapeutic treatments including other anti-tumor agents, and/or radiation therapy.

The pharmaceutical formulation may be administered via the parenteral route, including subcutaneously, intraperitoneally, intramuscularly, and intravenously. Examples of parenteral dosage forms include aqueous solutions of the active agent, in isotonic saline, 5% glucose, or other well-known pharmaceutically acceptable liquid carrier. In one preferred aspect of the present embodiment, the indenoisoquinolone or isoindoloisoquinolone compound is dissolved in a saline solution containing 5% dimethyl sulfoxide and 10% Cremphor EL (Sigma Chemical Company). Additional solubilizing agents such as cyclodextrins, which can form specific, more soluble complexes with the indenoisoquinolone or isoindoloisoquinolone compounds described herein, or other solubilizing agents well-known to those familiar with the art, can be utilized as pharmaceutical excipients for delivery of the indenoisoquinolone or isoindoloisoquinolone compounds.

The present compound can also be formulated into dosage forms for other routes of administration utilizing well-known methods. The pharmaceutical compositions can be formulated, for example, in dosage forms for oral administration in a capsule, a gel seal, or a tablet. Capsules may comprise any well-known pharmaceutically acceptable material such as gelatin or cellulose derivatives. Tablets may be formulated in accordance with conventional procedure by compressing mixtures of the active indenoisoquinoline or isoindoloisoquinoline and solid carriers, and lubricants well-known to those familiar with the art. Examples of solid carriers include starch, sugar, and bentonite. The compounds of the present invention can also be administered in a form of a hard shell tablet or capsule containing, for example, lactose or mannitol as a binder and conventional fillers and tableting agents.

The following examples are intended to illustrate various embodiments of the invention, and are not intended to in any way limit the scope of the invention as set forth in this specification and claims. Unless otherwise indicated, melting points were determined in capillary tubes and are uncorrected; Infrared spectra were obtained using CHCl$_3$ as the solvent; $^1$H NMR spectra were determined at 300 MHz using CDCl$_3$ as solvent and TMS as internal standard; microanalyses were performed at the Purdue University Microanalysis Laboratory; reactions were monitored by thin-layer chromatography (TLC) and visualized with short wavelength UV light; and compounds were purified by silica gel flash chromatography.

EXAMPLES

Example 1

General Synthesis of Compounds of formula II

Syntheses of the benzoisoindoloisoquinolone 8 and the analog compound 13, which lacks the two methoxyl groups of 8, are outlined in Scheme 1.

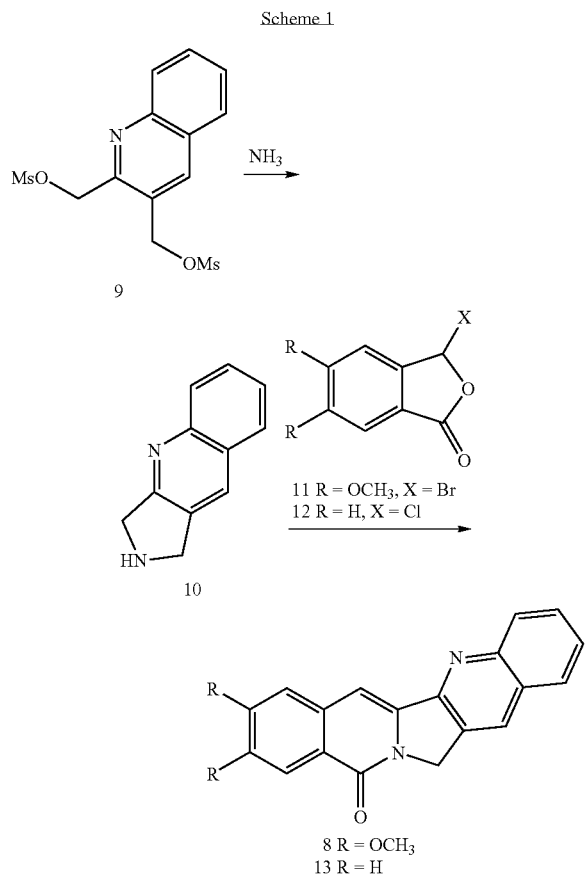

Treatment of a THF solution of the dimesylate 9 with liquid ammonia afforded the 2,3-dihydro-1H-pyrrolo[3,4-b] quinoline (10), which was reacted in situ with bromide 11 to afford the desired compound 8. Similarly, reaction of 10 with the chloride 12 yielded the corresponding unsubstituted derivative 13. Additional synthetic details and/or reaction conditions are generally described in Corey et al. in *J. Org. Chem.* 40:2140-41 (1975); Claus & Steinitz in *Justus Liebigs Ann. Chem.* 282:107-30 (1894); Parrick & Ragunathan in *J. Chem. Soc. Perkin Trans.* 1 211-16 (1993); Sloan & Koch in *J. Org. Chem.* 48:635-640 (1983), and Slemon et al. in *Can. J. Chem.* 59:3055-60 (1981), the disclosures of which are incorporated herein by reference. For example, the preparation of dimesylate 9 is described in Claus & Steinitz, the preparation of bromide 11 is described in Slemon et al., and the preparation of chloride 12 is described in Sloan & Koch.

Example 2

General Synthesis of Compounds of Formula I

As portrayed in Scheme 2, the 11-indenoisoquinolones 18-21 were prepared using a McMurry reaction of the ketone 2 with the haloaldehydes 14-17 (see Cushman & Cheng in *J. Org. Chem.* 43:3781-3783 (1978), the disclosure of which is incorporated herein by reference).

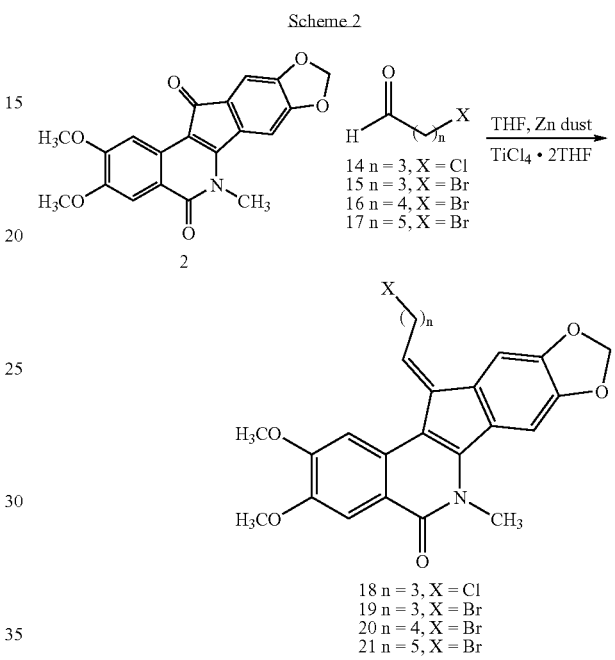

Figure 1:
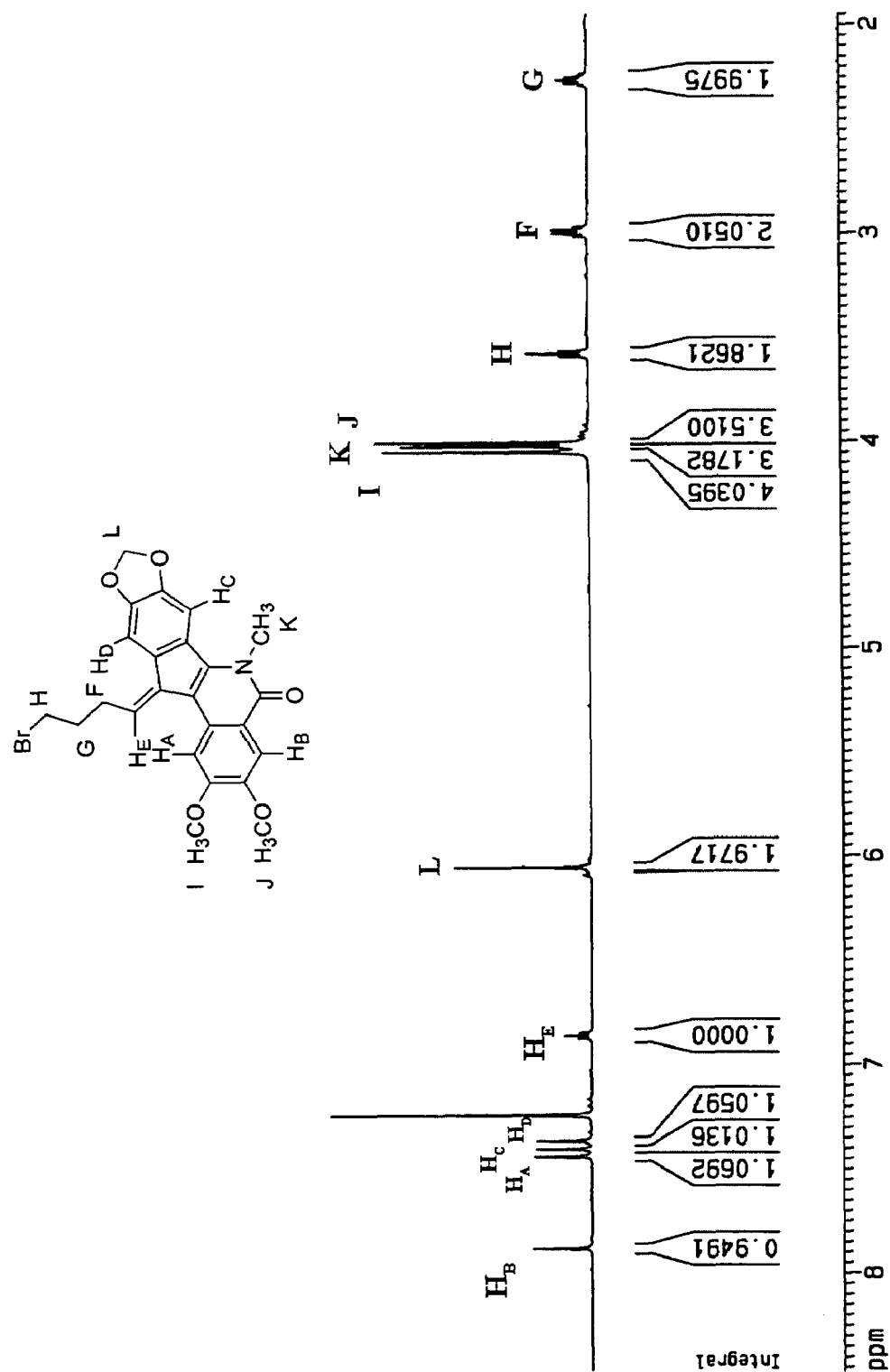
FIG. 1 shows a $^1$H NMR spectrum of indenoisoquinolone 19.

In each case, the production of a single double bond isomer was observed. The stereochemistry of the double bond was determined by obtaining nuclear Overhauser effect (NOE) difference spectra of compound 19. The interpretation of the NOE difference spectra is based on the assignments of the signals in the $^1$H NMR spectrum of 19 (FIG. 1). The $H_B$, $H_E$, L, F, G, and H protons were assigned to the resonances at 7.89, 6.86, 6.08, 3.00, 2.28, and 3.61 ppm, respectively (see FIG. 1). The resonance at 7.89 ppm was assigned to HB because this proton is adjacent to the amide carbonyl, which would presumably deshield $H_B$ and cause it to shift farthest downfield with respect to the other aromatic protons. The resonance at 6.68 ppm was assigned to the vinylic proton $H_E$ because this is the only triplet that might integrate for one proton. Furthermore, the resonance at 6.08 ppm was assigned to the L protons because they are the only protons that might appear as a two-proton singlet. The assignment of protons at F, G, and H was accomplished by evaluating their chemical shifts. The protons at H are adjacent to a bromide and are farthest downfield at 3.60 ppm. The allylic protons at F are further upfield at 3.00 ppm, and finally the protons at G are farthest upfield at 2.28 ppm.

The remaining aromatic resonances were assigned using NOE difference spectrometry. Irradiation of the L protons (6.08 ppm) resulted in enhancement of the resonances at 7.39 and 7.36 ppm, corresponding to $H_D$ and $H_C$. Because the resonance at 7.89 ppm was assigned to $H_B$, the resonance at 7.44 ppm should correspond to $H_A$ by the process of elimination. Irradiation of $H_E$ (6.86 ppm) resulted in a strong enhancement of the resonance at 7.44 ppm corresponding to $H_A$ instead of $H_D$. Therefore, the double bond at C-11 of indenoisoquinoline 4 supports the assigned E stereochemistry.

The assignments of the remainder of the resonances in the NMR spectrum of 19 (FIG. 1) were accomplished in the same manner and supported the assignments made above. Specifically, irradiation of the F protons (3.00 ppm) caused an enhancement of the resonance at 7.36 ppm. Therefore, the resonance at 7.36 ppm corresponds to $H_D$. Through the process of elimination, the resonance at 7.39 ppm must belong to $H_C$. Irradiation of $H_C$ (7.39 ppm) resulted in enhancement of the resonance at 4.040 ppm, resulting in assignment of this resonance to the protons of the methyl amine K. Finally, irradiation of $H_B$ (7.89 ppm) resulted in enhancement of the resonance at 4.023 ppm. Therefore, the resonance at 4.023 ppm corresponds to the protons at J, and by process of elimination, the resonance at 4.044 belongs to the protons at I.

Though as exemplified herein, the McMurry coupling reaction affords only the double bond having the E-double bond configuration, it is appreciated that the Z-double bond configuration or various mixtures of E and Z double bond isomers may be obtained using other conventional double bond forming reactions.

The 4-iodobutenyl compound 24 was derived from the bromide 19 using the Finkelstein reaction (Scheme 3).

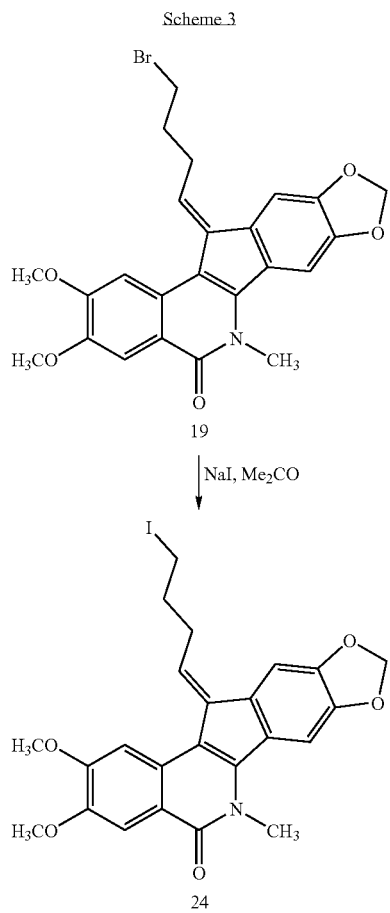

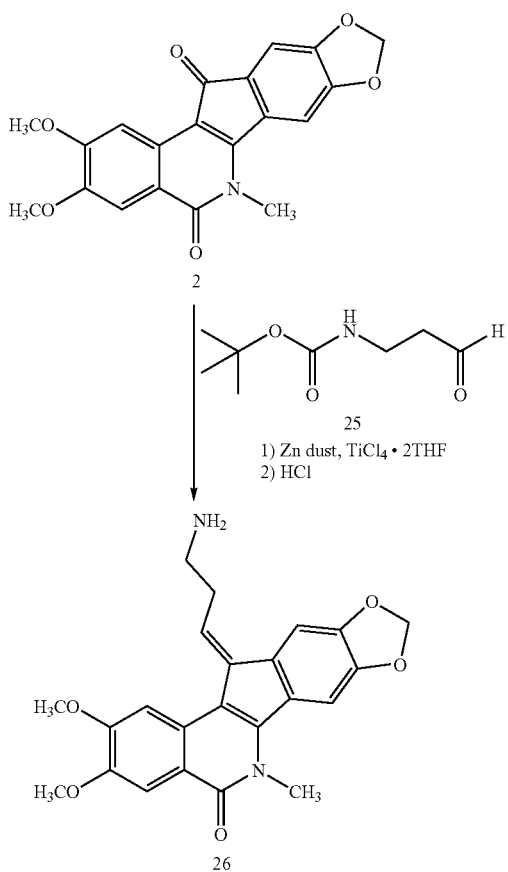

As with the haloalkene derivatives, the McMurry reaction of the lead compound 2 with Boc-protected β-alaninal (25) afforded the desired 3-aminopropenyl compound 26 after acidic work-up (Scheme 4).

Alaninal 25 may be prepared as described by Blaney et al, in *Tetrahedron* 58:1719-37 (2002), the disclosure of which is incorporated herein by reference.

Example 3

8,9-Dimethoxy-12H-5,11a-diaza-dibenzo[b,h]fluoren-11-one (8)

A solution of 9 (described in Claus & Steinitz, "Alkyl Derivatives of β-Quinaldic Acid," *Justus Liebigs Ann. Chem.*, 282, 107-130 (1894), the disclosure of which is incorporated herein by reference) (200 mg, 0.58 mmol) in anhydrous THF (20 mL) was degassed by bubbling argon through the solution for 30 min. Liquid $NH_3$ was added via cold finger for 5 min at approximately 1 drop/5 sec. The cold finger was removed and the reaction mixture was allowed to warm to room temperature under argon. The reaction mixture was stirred at room temperature for 12 h, at which point argon was bubbled through the solution for 1.5 h to remove excess $NH_3$. Anhydrous THF (10 mL) and $NEt_3$ (3 mL) were added and the reaction mixture was stirred at room temperature for 30 min. Bromide 11 (described in Slemon et al., "Synthesis of Phthalideisoquinolines from 3-Halopyridines and 3,4-Dihydroisoquinolinium Salts," *Can. J. Chem.*, 59, 3055-3060 (1981), the disclosure of which is incorporated herein by reference) was added and the reaction mixture was stirred at room temperature for 24 h. The solvent was removed in vacuo and replaced with 10% NaOAc/AcOH (30 mL). The reaction mixture was stirred at room temperature for 24 h, at which point the solvent was removed in vacuo. The resulting solid was dissolved in water (100 mL) and extracted with CHCl$_3$ (3×100 mL). The organic layers were pooled, washed with saturated aqueous NaHCO$_3$ (1×100 mL), brine, dried (MgSO$_4$), filtered, and concentrated in vacuo to provide a brown solid. Purification (silica gel, CHCl$_3$) provided 8 (106 mg, 53%) as a yellow solid: $^1$H NMR (300 MHz, DMSO-d$_6$) δ 8.61 (s, 1H), 8.12 (m, 2H), 7.84 (m, 1H), 7.71 (s, 1H), 7.82 (m, 1H), 7.61 (s, 1H), 7.50 (s, 1H), 5.32 (s, 2H), 3.94 (s, 3H), 3.91 (s, 3H); ESIMS m/z (rel intensity) 345.2 (100, MH$^+$). Anal. Calcd for C$_{21}$H$_{16}$N$_2$O$_3$.0.5H$_2$O: C, 71.38; H, 4.85; N, 7.93. Found: C, 71.07; H, 4.72; N, 7.85.

Example 4

12H-5,11a-Diaza-dibenzo[b,h]fluoren-11-one (13)

A solution of 9 (200 mg, 0.58 mmol) in anhydrous THF (20 mL) was degassed by bubbling argon through the solution for 30 min. Liquid NH$_3$ was added via cold finger for 5 min at approximately 1 drop/5 sec. The cold finger was removed and the reaction mixture was allowed to warm to room temperature under argon. The reaction mixture was stirred at room temperature for 12 h, at which point argon was bubbled through the solution for 1.5 h to remove excess NH$_3$, affording a solution of intermediate 10. Anhydrous THF (10 mL) and NEt$_3$ (3 mL) were added and the reaction mixture was stirred at room temperature for 30 min. Chloride 12 (Sloan & Koch, "Effect of Nucleophilicity and Leaving Group Ability on the S$_N$2 Reactions of Amines with (Acyloxy)alkyl α-Halides," *J. Org. Chem.*, 48, 635-640 (1983), the disclosure of which is incorporated herein by reference) (195 mg, 1.16 mmol) was added and the reaction mixture stirred at room temperature for 24 h. The solvent was removed in vacuo and replaced with 10% NaOAc/AcOH (30 mL). The reaction mixture was stirred at room temperature for 24 h, at which point the solvent was removed in vacuo. The resulting solid was dissolved in water (100 mL) and extracted with CHCl$_3$ (3×100 mL). The organic layers were pooled, washed with saturated aqueous NaHCO$_3$ (1×100 mL), brine, dried (MgSO$_4$), filtered, and concentrated in vacuo to provide a brown solid. Purification (silica gel, CHCl$_3$) provided 13 (90 mg, 55%) as a yellow solid: IR (film) 3062, 2952, 2839, 1714, 1619, 1566, 1456, 1438, 1256, 1067 cm$^{-1}$; $^1$H NMR (300 MHz, CDCl$_3$) δ 8.56 (d, J=7.56 Hz, 1H), 8.34 (s, 1H), 8.23 (d, J=8.64 Hz, 1H), 7.91 (d, J=8.19 Hz, 1H), 7.90-7.71 (m, 3H), 7.68 (s, 1H), 7.66-7.56 (m, 2H), 5.38 (d, J=1.07 Hz, 2H); ESIMS m/z (rel intensity) 285.2 (100, MH$^+$). Anal. Calcd for C$_{19}$H$_{12}$N$_2$O.0.25H$_2$O: C, 79.01; H, 5.46; N, 9.70. Found: C, 79.30; H, 5.36; N, 9.66.

Example 5

11-(4'-Chlorobutylidene)-5,6-dihydro-2,3-dimethoxy-6-methyl-8,9-methylenedioxy-5-oxo-11H-indeno[1,2-c]isoquinoline (18)

TiCl$_4$.2THF (508 mg, 1.52 mmol), Zn dust (199 mg, 3.04 mmol), and dry THF (15 mL) were added to a flame-dried two-necked flask equipped with a magnetic stir bar and reflux condenser. The suspension was heated at reflux under argon for 3 h, after which a solution of 4-chlorobutanal (14) (Li et al., "Synthesis of the Tricyclic ABC Ring Subunit of Mazamine A," *Tetrahedron*, 54, 6661-6676 (1998), the disclosure of which is incorporated herein by reference) (108.1 mg, 1.01 mmol) and indenoisoquinoline 2 (185 mg, 0.51 mmol) in dry THF (15 mL) was introduced by syringe. The reaction mixture was heated at reflux for 2.5 h, after which 4 N HCl (20 mL) was added. The solution was stirred at room temperature for 1 h and then allowed to stand for 3 h. The resulting orange precipitate was collected by vacuum filtration. The solid was purified by flash chromatography (silica gel, 5:1 CHCl$_3$/hexanes) to provide 18 (96.1 mg, 43%) as an orange solid: mp 196-201° C.; IR (film) 2926, 1636, 1610, 1517, 1483, 1255, 1034 cm$^{-1}$; $^1$H NMR (300 MHz, CDCl$_3$) δ 7.89 (s, 1H), 7.78 (s, 1H), 7.40 (s, 1H), 7.37 (s, 1H), 6.88 (t, J=7.19 Hz, 1H), 6.04 (s, 2H), 4.05 (s, 3H), 4.03 (s, 3H), 4.02 (s, 3H), 3.74 (t, J=6.32 Hz, 2H), 3.00 (dt, J=7.30 and 7.45 Hz, 2H), 2.20 (qn, J=6.90 Hz, 2H); ESIMS m/z (rel intensity) 440.7 (100, MH$^+$), 442.6 (43, MH$^+$). Anal. Calcd for C$_{24}$H$_{22}$ClNO$_5$: C, 65.53; H, 5.04; N, 3.18. Found: C, 65.30; H, 4.96; N, 3.08.

Example 6

11-(4'-Bromobutylidene)-5,6-dihydro-2,3-dimethoxy-6-methyl-8,9-methylenedioxy-5-oxo-11H-indeno[1,2-c]isoquinoline (19)

A 100 mL two-necked round-bottomed flask equipped with a magnetic stirring bar, reflux condenser, septa, and argon line was charged with zinc dust (537 mg, 8.21 mmol) and was flame dried. THF (30 mL) and a 1 M solution of TiCl$_4$ in toluene (4.11 mL, 4.11 mmol) were added. The suspension was heated at reflux for 5 h, at which point a suspension of 2 (500 mg, 1.37 mmol) and 4-bromobutanal (15) (Canan Koch & Chamberlin, "Enantioselective Preparation of β-Alkyl-γ-butyrolactones from Functionalized Ketene Dithioacetals," *J. Org. Chem.*, 58, 2725-2737 (1993); Somekawa et al., "Intramolecular [2+2]Photocycloadditions of 1-(ω-Alkenyl)-2-pyridones Possessing an Ester Group on the Olefinic Carbon Chain," *J. Org. Chem*, 57, 5708-5712, (1992), the disclosures of which are incorporated herein by reference) (413 mg, 2.74 mmol) in THF (30 mL) was added by pipette. The reaction mixture was heated at reflux for 1 h and then quenched with 4 N HCl (40 mL). The solution was stirred for 1 h and then cooled at 0° C. for 2 h. The orange precipitate was collected by vacuum filtration to provide an orange solid. This was purified by flash chromatography (silica gel, CHCl$_3$) to provide 19 (161.6 mg, 30%) as an orange solid: mp 197-199° C.; IR (film) 2921, 1610, 1517, 1483, 1381, 1296, 1253, 1207, 1033 cm$^{-1}$; $^1$H NMR (500 MHz, CDCl$_3$) δ 7.88 (s, 1H), 7.44 (s, 1H), 7.40 (s, 1H), 7.36 (s, 1H), 6.83 (t, J=7.11 Hz, 1H), 6.05 (s, 2H), 4.00 (s, 6H), 3.97 (s, 3H), 3.57 (t, J=6.33 Hz, 2H), 2.97 (q, J=7.23 Hz, 2H), 2.25 (qn, J=6.80 Hz, 2 H); ESIMS m/z (rel intensity) 486.2 (97, MH$^+$), 484.2 (100, MH$^+$). Anal. Calcd for C$_{24}$H$_{22}$BrNO$_5$: C, 59.52; H, 4.58; N, 2.89. Found: C, 59.56; H, 4.56; N, 2.88.

Example 7

11-(5'-Bromopentylidene)-5,6-dihydro-2,3-dimethoxy-6-methyl-8,9-methylenedioxy-5-oxo-11H-indeno[1,2-c]isoquinoline (20)

A 100 mL two-necked round-bottomed flask equipped with a reflux condenser and magnetic stir bar was charged with zinc dust (537 mg, 8.21 mmol) and flame dried. THF (30 mL) and 1 M TiCl$_4$ in toluene (4.11 mL, 4.11 mmol) were added to the round-bottomed flask and the mixture was heated at reflux for 6 h. THF (30 mL), 5-bromopentanal (16) (452 mg, 2.74 mmol) and 2 (500 mg 1.37 mmol) were added to the reaction mixture, which was heated at reflux for 2 h. The reaction mixture was cooled to room temperature, 4 N HCl (40 mL) was added, and this mixture was stirred for 30 min and cooled in a −20° C. freezer overnight. The resulting yellow precipitate was collected by vacuum filtration and purified by flash chromatography to provide 20 (133.7 mg, 33%) as an orange solid: mp 196-197° C.; IR (film) 2932, 1632, 1612, 1517, 1483, 1254, 1032 cm$^{-1}$; $^1$H NMR (500 MHz, CDCl$_3$) δ 7.89 (s, 1H), 7.46 (s, 1H), 7.41 (s, 1H), 7.32 (s, 1H), 6.86 (t, J=6.83 Hz, 1H), 6.05 (s, 2H), 4.05 (s, 3H), 4.03 (s, 3H), 4.01 (s, 3H), 3.49 (t, J=6.47 Hz, 2 H), 2.86 (q, J=7.15 Hz, 2H), 2.06 (m, 2H), 1.88 (m, 2H); ESIMS m/z (rel intensity) 1500.2 (95, MH$^+$), 498.2 (100, MH$_+$). Anal. Calcd for $C_{25}H_{24}BrNO_5$: C, 60.25; H, 4.85; N, 2.81. Found: C, 60.57; H, 4.90; N, 2.83.

Example 8

11-(6'-Bromohexylidene)-5,6-dihydro-2,3-dimethoxy-6-methyl-8,9-methylenedioxy-5-oxo-11H-indeno[1,2-c]isoquinoline (21)

A 100 mL two-necked round-bottomed flask equipped with a reflux condenser and magnetic stir bar was charged with zinc dust (537 mg, 8.21 mmol) and flame dried. THF (30 mL) and 1 M TiCl$_4$ in toluene (4.11 mL, 4.11 mmol) were added to the round-bottomed flask and the mixture was heated at reflux for 4 h. Anhydrous THF (30 mL), 6-bromohexanal (17) (491 mg, 2.74 mmol) and 2 (500 mg 1.37 mmol) were added to the reaction mixture, which was heated at reflux for 2 h. The reaction mixture was cooled to room temperature, 4 N HCl (40 mL) was added, and this mixture was stirred for 30 min and then cooled in a −20° C. freezer overnight. The resulting yellow precipitate was collected by vacuum filtration and purified by flash chromatography to provide 21 (118.0 mg, 17%) as an orange solid: mp 182-185° C.; IR (film) 2929, 1636, 1610, 1516, 1482, 1296, 1255, 1033 cm$^{-1}$; $^1$H NMR (500 MHz, CDCl$_3$) δ 7.88 (s, 1H), 7.46 (s, 1H), 7.40 (s, 1H), 7.32 (s, 1H), 6.88 (t, J=6.96 Hz, 1H), 6.05 (s, 2H), 4.06 (s, 3H), 4.02 (s, 3H), 4.00 (s, 3H), 3.44 (t, J=6.62 Hz, 2H), 2.84 (q, J=7.13 Hz, 2H), 1.95 (qn, J=7.04 Hz, 2H), 1.74 (m, 2H) 1.66 (m, 2H); ESIMS m/z (rel intensity) 514.2 (100, MH$^+$), 512.2 (91, MH$^+$). Anal. Calcd for $C_{26}H_{26}BrNO_5$: C, 60.95; H, 5.11; N, 2.73. Found: C, 60.55; H, 5.08; N, 2.72.

Example 9

11-(4'-Iodobutylidene)-5,6-dihydro-2,3-dimethoxy-6-methyl-8,9-methylenedioxy-5-oxo-11H-indeno[1,2-c]isoquinoline (24)

NaI (217 mg, 1.45 mmol) was added to a suspension of bromide 19 (70 mg, 0.15 mmol) in acetone (15 mL). The reaction mixture was heated at reflux for 12 h, after which the resulting orange precipitate was collected by vacuum filtration and purified by flash chromatography (silica gel, CHCl$_3$) to provide 24 (73.0 mg, 95%) as an orange solid: mp 173-174.5° C.; IR (KBr) 2944, 1612, 1522, 1481, 1254, 1033 cm$^{-1}$; $^1$H NMR (500 MHz, CDCl$_3$) δ 7.88 (s, 1H), 7.43 (s, 1H), 7.40 (s, 1H), 7.36 (s, 1 H), 6.84 (t, J=7.22 Hz, 1H), 6.05 (s, 2H), 4.08 (s, 3H), 4.04 (s, 3H), 4.00 (s, 3H), 3.35 (t, J=6.69 Hz, 2H), 2.95 (q, J=7.32 Hz, 2H), 2.19 (m, 2H); ESIMS m/z (rel intensity) 532.1 (100, MH$_+$). Anal. Calcd for $C_{24}H_{22}INO_5$: C, 54.25; H, 4.17; N, 2.64. Found: C, 54.64; H, 4.25; N, 2.60.

Example 10

11-(3'-Aminopropylidene)-5,6-dihydro-2,3-dimethoxy-6-methyl-8,9-methylenedioxy-5-oxo-11H-indeno[1,2-c]isoquinoline (26)

TiCl$_4$-THF (1:2) complex (730 mg, 2.19 mmol) and zinc dust (284 mg, 4.37 mmol) were put in a three-necked round-bottomed flask. THF (30 mL) was added. The resulting suspension was heated under reflux for 4 h. At this point, a mixture of aldehyde 25 (Blaney et al., "Fused and Bridged Bi- and Tri-Cyclic Lactams via Sequential Metallo-Azomethine Ylide Cycloaddition-Lactamisation," *Tetrahedron*, 58, 1719-37 (2002), the disclosures of which are incorporated herein by reference) (189 mg, 1.09 mmol) and indenoisoquinoline 2 (266 mg, 0.73 mmol) in THF (30 mL) was added via syringe. The reaction mixture was stirred under reflux for an additional 4 h. Then 3 N HCl (10 mL) was added after cooling to room temperature and the mixture was stirred at room temperature for 1 h, followed by 0° C. for 2 h, and finally at room temperature overnight. The mixture was cooled to 0° C. and solid NaHCO$_3$ was added to neutralize HCl. The solvents were evaporated and the residue was subjected to flash chromatography, eluting with CHCl$_3$-MeOH (4:1) to provide 26 as a yellow powder (121 mg, 41%): mp>180° C. (dec); $^1$H NMR (300 MHz, DMSO-d$_6$) 7.68 (s, 1H), 7.62 (s, 1H), 7.51 (s, 1H), 7.48 (s, 1H), 6.94 (t, J=6.0 Hz, 1H), 6.15 (s, 2H), 4.01 (s, 3H), 3.95 (s, 3H), 3.87 (s, 3H), 3.12-3.18 (m, 4 H). ESIMS m/z (rel intensity) 407.0 (100, MH$^+$). Anal. Calcd for $C_{23}H_{22}N_2O_5 \cdot 0.9CHCl_3$: C, 55.86; H, 4.49; N, 5.45. Found: C, 55.86; H, 4.72; N, 5.24.

Example 11

Top1-Mediated DNA Cleavage Reactions

Human recombinant top1 was purified from Baculovirus as described by Pourquier et al. in *J. Biol. Chem.* 274:8516-23 (1999), the disclosure of which is incorporated herein by reference. The 161 bp fragment from pBluescript SK(−) phagemid DNA (Stratagene, La Jolla, Calif.) was cleaved with the restriction endonuclease Pvu II and Hind III (New England Biolabs, Beverly, Mass.) in supplied NE buffer 2 (10 μL reactions) for 1 h at 37° C., and separated by electrophoresis in a 1% agarose gel made in 1×TBE buffer. The 161 bp fragment was eluted from the gel slice (centrilutor by Amicon) and concentrated in a centricon 50 centrifugal concentrator (Amicon, Beverly, Mass.). Approximately 200 ng of the fragment was 3'-end labeled at the Hind III site by fill-in reaction with [alpha-$^{32}$P]-dGTP and 0.5 mM dATP, dCTP, and dTTP, in React 2 buffer (50 mM Tris-HCl, pH 8.0, 100 mM MgCl$_2$, 50 mM NaCl) with 0.5 units of DNA polymerase I (Klenow fragment). Unincorporated $^{32}$P-dGTP was removed using mini Quick Spin DNA columns (Roche, Indianapolis, Ind.), and the eluate containing the 3'-end-labeled 161 bp fragment was collected. Aliquots (approximately 50,000 dpm/reaction) were incubated with top1 at 22° C. for 30 min in the presence of the tested drug. Reactions were terminated by adding SDS (0.5% final concentration). The samples (10 μL) were mixed with 30 μL of loading buffer (80% formamide, 10 mM sodium hydroxide, 1 mM sodium EDTA, 0.1% xylene cyanol, and 0.1% bromophenol blue, pH 8.0). Aliquots were separated in denaturing gels (16% polyacrylamide, 7 M urea). Gels were dried and visualized by using a Phosphoimager and ImageQuant software (Molecular Dynamics, Sunnyvale, Calif.).

Selected indenoisoquinolones described herein were examined for antiproliferative activity against the human cancer cell lines in the National Cancer Institute screen, in which the activity of each compound was evaluated with approximately 55 different cancer cell lines of diverse tumor origins. The mean graph midpoint (MGM) shown in Table 1 is based on a calculation of the average GI50 for all of the approximately 55 cell lines tested, where GI50 values below and above the test range ($10^{-8}$ to $10^{-4}$ molar) are taken as the minimum ($10^{-8}$ molar) and maximum ($10^{-4}$ molar) drug concentrations used in the screening test. The GI50 values obtained from selected cell lines for these indenoisoquinolones are also summarized in Table 1. The relative activities of selected indenoisoquinolines described herein were obtained from the top 1-mediated DNA cleavage assay, and are also shown in Table 1. Compounds 2 and 7 are also included the Table 1.

Example 12

Biological Activity of Compounds of formula I

The halogenated 11-alkenyl side chain derivatives 18-21 and 24 were all approximately in the same range of cytotoxicity as compound 2. However, compounds 21 and 24 were slightly more cytotoxic than compounds 18-20. In addition, the five-carbon bromide 20 and the six-carbon bromide 21 showed higher inhibitory activity against top1 than the four-carbon alkenyl halides 19 and 24.

The most potent compound in the present series of new indenoisoquinolines, both in terms of cytotoxicity and top1 inhibitory activity, was the compound 26. having a cytotoxicity mean graph midpoint (MGM) of 0.34 µM, indicating a large increase in overall cytotoxicity in cancer cell cultures. In addition, the resulting compound 26 was more potent as a top1 poison than compound 2.

Without being bound by theory, a hydrogen bonding interaction between the hydroxyl group of the camptothecin analogue topotecan and the carboxyl group of Asp533 of the enzyme may contribute to the binding of the camptothecin ring system. Similarly, the 3'-aminopropenyl side chain in compound 26 may project into the minor groove, where it might possibly interact with Asp533 or Arg364, or with a stacked base residue of the DNA.

It is appreciated that cytotoxicity profile of compounds described herein may be improved by altering solubility properties, facilitating cellular uptake, and/or the inclusion of components that take advantage of the electrostatic attraction of a positively charged ammonium cation to a negatively charged DNA phosphodiester backbone prior to intercalation into the cleavage complex, as illustrated by compounds 26 and 7.

Example 13

Biological Activity of Compounds of Formula II

Both compounds 8 (MGM 91.2 µM) and 13 (MGM 58.9 µM) were generally less cytotoxic than compound 2 (MGM 20.0 µM). The hybrid molecule 13 and the lead compound 2 displayed similar potencies as top1 inhibitors. It was observed that the pattern of top1-mediated DNA cleavage sites induced by 13 better resembled that of compound 2 than that of camptothecin, though the only difference between camptothecin (3) and analogues 8 and 13 was the replacement of the lactone ring of camptothecin (3) by either the dimethoxybenzene ring in 8 or the benzene ring in 13.

Example 14

Figure 2:
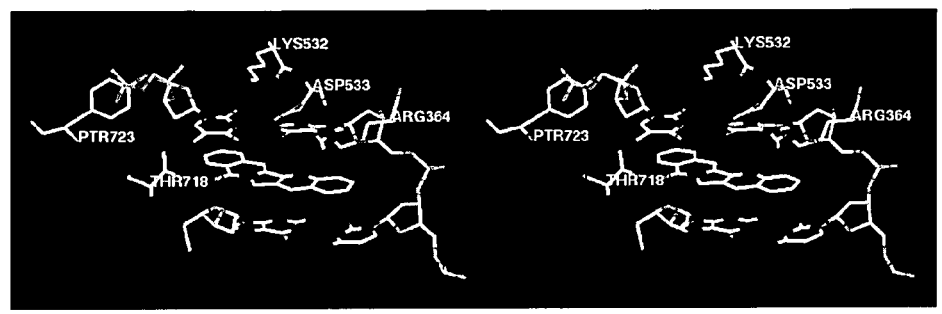
FIG. 2 shows a model of the binding of isoindoloisoquinolone 13 in a ternary complex comprising DNA, top1, and the inhibitor. The diagram is programmed for wall-eyed viewing.
Figure 3:
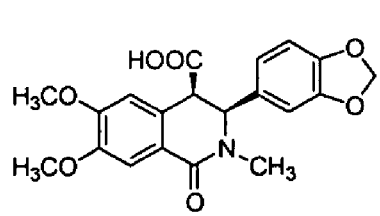
FIG. 3 shows various indenoisoquinolones, isoindoloisoquinolones, and derivatives thereof.
Figure 3:
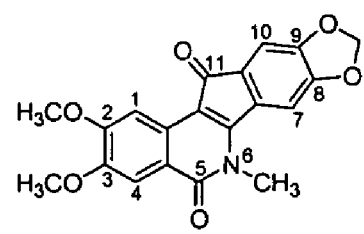
Figure 3:
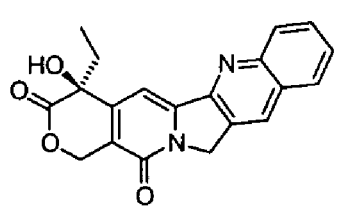
Figure 3:
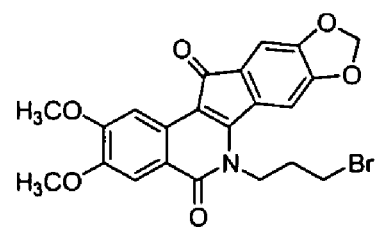
Figure 3:
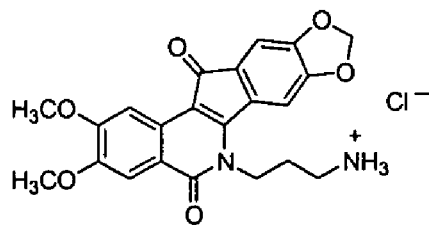
Figure 3:
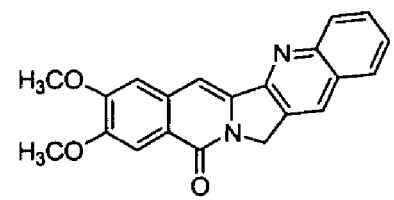

Computer Model of the Ternary Complex Consisting of DNA, Top1, and Compounds of Formula II To investigate the nature of the binding of compound 13 in the published ternary complex, a model was constructed by overlapping the structure of the hybrid 13 with the structure of topotecan in the published ternary complex (see Staker et al. in *Proc. Natl. Acad. Sci. U.S.A.* 99:15387-15392 (2002), the disclosure of which is incorporated herein by reference) and then deleting the camptothecin structure (FIG. 2). It was reported that the synthetic double-stranded DNA in the crystalline ternary complex contained a phosphorothiolate at the cleavage site. Compound 13 can be modeled into the camptothecin binding site in the ternary complex without any obvious steric constraints.

TABLE 1

Cytotoxicities and Topoisomerase I Inhibitory Activities of Indenoisoquinoline Analogs.[a]

| compd | lung HOP-62 | colon HCT-116 | CNS SF-539 | melanoma UACC-62 | ovarian OVCAR-3 | renal SN12C | prostate DU-145 | breast MDA-MB-435 | MGM[b] | Top 1 Cleavage[c] |
|---|---|---|---|---|---|---|---|---|---|---|
| 8 | >100 | 57.3 | >100 | >100 | >100 | >100 | >100 | >100 | 91.2 | + |
| 13 | 68.2 | 32.7 | 66.7 | 97.2 | 39.8 | >100 | >100 | 41.8 | 58.9 | ++ |
| 18 | 17.5 | 40.4 | NT[d] | 33.3 | 42.3 | >100 | 35.9 | >100 | 33.1 | + |
| 19 | 19.4 | 37.8 | 30.0 | 11.4 | 58.1 | >100 | 67.8 | >100 | 27.8 | 0 |
| 20 | 26.6 | 9.5 | 7.1 | >100 | >100 | >100 | 4.5 | >100 | 33.1 | ± |
| 21 | 3.1 | 6.1 | 5.7 | 3.9 | 23.6 | 5.7 | 5.5 | 19.2 | 7.8 | + |
| 24 | 27.6 | 0.56 | 4.3 | 3.5 | 22.8 | 8.8 | 28.7 | 5.2 | 16.8 | 0 |
| 26 | 0.071 | 0.028 | 0.42 | 0.20 | 0.56 | 0.58 | 0.37 | 1.8 | 0.34 | +++ |
| 2 | 1.3 | 35 | 41 | 4.2 | 73 | 68 | 37 | 96 | 20 | ++ |
| 7 | 0.06 | 0.13 | 0.26 | 0.25 | 0.31 | 0.31 | 0.04 | 1.21 | 0.16 | +++ |

[a]The cytotoxicity (GI50) values were the concentrations (µM) corresponding to 50% growth inhibition.
[b]Mean graph midpoint for growth inhibition of all human cancer cell lines successfully tested.
[c]The compounds were tested at concentrations ranging up to 10 µM; the activity of the compounds to produce top1-mediated DNA cleavage is expressed as follows: weak activity (+), activity similar to compound 2 (++), activity greater than compound 2 (+++).

The invention claimed is:
1. A compound of the formula:

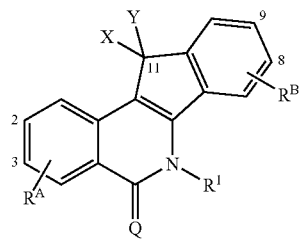

wherein

Q is oxygen or sulfur;

X is hydrogen and Y is NHOR$^2$, or NHNR$^2$R$^3$; or X and Y are taken together to form =CR$^2$R$^3$; =NR$^2$; =NOR$^2$; or =NNR$^2$R$^3$;

R$^1$, R$^2$, and R$^3$ are each independently selected from the group consisting of hydrogen and a radical —(CH$_2$)$_m$Z, where m is an integer from 0-6 and Z is selected from the group consisting of halogen, hydroxy, formyl, C$_1$-C$_6$ alkanoyloxy, optionally substituted benzoyloxy, C$_1$-C$_6$ alkyl, C$_1$-C$_6$ alkoxy, C$_3$-C$_8$ cycloalkyl, C$_3$-C$_8$ cycloalkoxy, C$_2$-C$_6$ alkenyl, C$_2$-C$_6$ alkynyl, C$_1$-C$_6$ haloalkyl, C$_1$-C$_6$ haloalkoxy, C$_3$-C$_8$ halocycloalkyl, C$_3$-C$_8$ halocycloalkoxy, amino, C$_1$-C$_6$ alkylamino, (C$_1$-C$_6$ alkyl)(C$_1$-C$_6$ alkyl)amino, alkylcarbonylamino, N—(C$_1$-C$_6$ alkyl)alkylcarbonylamino, aminoalkyl, C$_1$-C$_6$ alkylaminoalkyl, (C$_1$-C$_6$ alkyl)(C$_1$-C$_6$ alkyl)aminoalkyl, alkylcarbonylaminoalkyl, N—(C$_1$-C$_6$ alkyl)alkylcarbonylaminoalkyl, cyano, nitro, C$_1$-C$_6$ alkylsulfonyl, optionally substituted phenyl, optionally substituted phenoxy, and optionally substituted heteroaryl; or Z is selected from the group consisting of —N$_3$, —CO$_2$R$^4$, —CONR$^5$R$^6$, —P(O)(OR$^4$)$_2$, —P(O)(NR$^4$R$^5$)$_2$, and —P(O)(NR$^4$R$^5$)(OR$^4$), where R$^4$, R$^5$, and R$^6$ are each independently selected in each occurrence from the group consisting of hydrogen, C$_1$-C$_6$ alkyl, C$_3$-C$_8$ cycloalkyl, C$_1$-C$_6$ haloalkyl, optionally substituted phenyl, and optionally substituted phenyl-C$_1$-C$_6$ alkyl; or when X and Y are taken together to form =NNR$^2$R$^3$, R$^2$ and R$^3$ are taken together with the attached nitrogen to form an optionally substituted heterocycle;

providing that Y and R$^1$ are not both alkyl;

R$^A$ represents 1-4 substituents each independently selected from the group consisting of hydrogen and a radical —(CH$_2$)$_{m'}$Z', where m' is an integer from 0-6 and Z' is selected from the group consisting of halogen, hydroxy, C$_1$-C$_6$ alkanoyloxy, optionally substituted benzoyloxy, C$_1$-C$_6$ alkyl, C$_1$-C$_6$ alkoxy, C$_3$-C$_8$ cycloalkyl, C$_3$-C$_8$ cycloalkoxy, C$_2$-C$_6$ alkenyl, C$_2$-C$_6$ alkynyl, C$_1$-C$_6$ haloalkyl, C$_1$-C$_6$ haloalkoxy, C$_3$-C$_8$ halocycloalkyl, C$_3$-C$_8$ halocycloalkoxy, amino, C$_1$-C$_6$ alkylamino, (C$_1$-C$_6$ alkyl)(C$_1$-C$_6$ alkyl)amino, alkylcarbonylamino, N—(C$_1$-C$_6$ alkyl)alkylcarbonylamino, aminoalkyl, C$_1$-C$_6$ alkylaminoalkyl, (C$_1$-C$_6$ alkyl)(C$_1$-C$_6$ alkyl)aminoalkyl, alkylcarbonylaminoalkyl, N—(C$_1$-C$_6$ alkyl)alkylcarbonylaminoalkyl, cyano, nitro, C$_1$-C$_6$ alkylsulfonyl, optionally substituted phenyl, optionally substituted phenoxy, and optionally substituted heteroaryl; or Z' is selected from the group consisting of —N$_3$, —CO$_2$R$^{4'}$, —CONR$^{5'}$R$^{6'}$, —P(O)(OR$^{4'}$)$_2$, —P(O)(NR$^{4'}$R$^{5'}$)$_2$, and —P(O)(NR$^{4'}$R$^{5'}$)(OR$^{4'}$), where R$^{4'}$, R$^{5'}$, and R$^{6'}$ are each independently selected in each occurrence from the group consisting of hydrogen, C$_1$-C$_6$ alkyl, C$_3$-C$_8$ cycloalkyl, C$_1$-C$_6$ haloalkyl, optionally substituted phenyl, and optionally substituted phenyl-C$_1$-C$_6$ alkyl; or R$^A$ represents 2-4 substituents where 2 of said substituents are adjacent substituents and are taken together with the attached carbons to form an optionally substituted carbocycle or an optionally substituted heterocycle, and the remaining 2 substituents are each independently selected from the group consisting of hydrogen and a radical —(CH$_2$)$_{m'}$Z', where m' is an integer from 0-6 and Z' is selected from the group consisting of halogen, hydroxy, C$_1$-C$_6$ alkanoyloxy, optionally substituted benzoyloxy, C$_1$-C$_6$ alkyl, C$_1$-C$_6$ alkoxy, C$_3$-C$_8$ cycloalkyl, C$_3$-C$_8$ cycloalkoxy, C$_2$-C$_6$ alkenyl, C$_2$-C$_6$ alkynyl, C$_1$-C$_6$ haloalkyl, C$_1$-C$_6$ haloalkoxy, C$_3$-C$_8$ halocycloalkyl, C$_3$-C$_8$ halocycloalkoxy, amino, C$_1$-C$_6$ alkylamino, (C$_1$-C$_6$ alkyl)(C$_1$-C$_6$ alkyl)amino, alkylcarbonylamino, N—(C$_1$-C$_6$ alkyl)alkylcarbonylamino, aminoalkyl, C$_1$-C$_6$ alkylaminoalkyl, (C$_1$-C$_6$ alkyl)(C$_1$-C$_6$ alkyl)aminoalkyl, alkylcarbonylaminoalkyl, N—(C$_1$-C$_6$ alkyl)alkylcarbonylaminoalkyl, cyano, nitro, C$_1$-C$_6$ alkylsulfonyl, optionally substituted phenyl, optionally substituted phenoxy, and optionally substituted heteroaryl; or Z' is selected from the group consisting of —N$_3$, —CO$_2$R$^{4'}$, —CONR$^{5'}$R$^{6'}$, —P(O)(O$^{4'}$)$_2$, —P(O)(NR$^{4'}$R$^{5'}$)$_2$, and —P(O)(NR$^{4'}$R$^{5'}$)(OR$^{4'}$), where R$^{4'}$, R$^{5'}$, and R$^{6'}$ are each independently selected in each occurrence from the group consisting of hydrogen, C$_1$-C$_6$ alkyl, C$_3$-C$_8$ cycloalkyl, C$_1$-C$_6$ haloalkyl, optionally substituted phenyl, and optionally substituted phenyl-C$_1$-C$_6$ alkyl; and R$^B$ represents 1-4 substituents each independently selected from the group consisting of hydrogen and a radical —(CH$_2$)$_{m''}$Z'', where m'' is an integer from 0-6 and Z'' is selected from the group consisting of halogen, hydroxy, C$_1$-C$_6$ alkanoyloxy, optionally substituted benzoyloxy, C$_1$-C$_6$ alkyl, C$_1$-C$_6$ alkoxy, C$_3$-C$_8$ cycloalkyl, C$_3$-C$_8$ cycloalkoxy, C$_2$-C$_6$ alkenyl, C$_2$-C$_6$ alkynyl, C$_1$-C$_6$ haloalkyl, C$_1$-C$_6$ haloalkoxy, C$_3$-C$_8$ halocycloalkyl, C$_3$-C$_8$ halocycloalkoxy, amino, C$_1$-C$_6$ alkylamino, (C$_1$-C$_6$ alkyl)(C$_1$-C$_6$ alkyl)amino, alkylcarbonylamino, N—(C$_1$-C$_6$ alkyl)alkylcarbonylamino, aminoalkyl, C$_1$-C$_6$ alkylaminoalkyl, (C$_1$-C$_6$ alkyl)(C$_1$-C$_6$ alkyl)aminoalkyl, alkylcarbonylaminoalkyl, N—(C$_1$-C$_6$ alkyl)alkylcarbonylaminoalkyl, cyano, nitro, C$_1$-C$_6$ alkylsulfonyl, optionally substituted phenyl, optionally substituted phenoxy, and optionally substituted heteroaryl; or Z'' is selected from the group consisting of —N$_3$, —CO$_2$R$^{4''}$, —CONR$^{5''}$R$^{6''}$, —P(O)(OR$^{4''}$)$_2$, —P(O)(NR$^{4''}$R$^{5''}$)$_2$, and —P(O)(NR$^{4''}$R$^{5''}$)(OR$^{4''}$), where R$^{4''}$, R$^{5''}$, and R$^{6''}$ are each independently selected in each occurrence from the group consisting of hydrogen, C$_1$-C$_6$ alkyl, C$_3$-C$_8$ cycloalkyl, C$_1$-C$_6$ haloalkyl, optionally substituted phenyl, and optionally substituted phenyl-C$_1$-C$_6$ alkyl; or R$^B$ represents 2-4 substituents where 2 of said substituents are adjacent substituents and are taken together with the attached carbons to form an optionally substituted carbocycle or an optionally substituted heterocycle, and the remaining 2 substituents are each independently selected from the group consisting of hydrogen and a radical —(CH$_2$)$_{m''}$Z'', where m'' is an integer from 0-6 and Z'' is selected from the group consisting of halogen, hydroxy, C$_1$-C$_6$ alkanoyloxy, optionally substituted benzoyloxy, C$_1$-C$_6$ alkyl, C$_1$-C$_6$ alkoxy, C$_3$-C$_8$ cycloalkyl, $C_3$-$C_8$ cycloalkoxy, $C_2$-$C_6$ alkenyl, $C_2$-$C_6$ alkynyl, $C_1$-$C_6$ haloalkyl, $C_1$-$C_6$ haloalkoxy, $C_3$-$C_8$ halocycloalkyl, $C_3$-$C_8$ halocycloalkoxy, amino, $C_1$-$C_6$ alkylamino, ($C_1$-$C_6$ alkyl)($C_1$-$C_6$ alkyl)amino, alkylcarbonylamino, N—($C_1$-$C_6$ alkyl)alkylcarbonylamino, aminoalkyl, $C_1$-$C_6$ alkylaminoalkyl, ($C_1$-$C_6$ alkyl)($C_1$-$C_6$ alkyl)aminoalkyl, alkylcarbonylaminoalkyl, N—($C_1$-$C_6$ alkyl)alkylcarbonylaminoalkyl, cyano, nitro, $C_1$-$C_6$ alkylsulfonyl, optionally substituted phenyl, optionally substituted phenoxy, and optionally substituted heteroaryl; or Z″ is selected from the group consisting of —$N_3$, —$CO_2R^{4″}$, —$CONR^{5″}R^{6″}$, —$P(O)(OR^{4″})_2$, —$P(O)(NR^{4″}R^{5″})_2$, and —$P(O)(NR^{4″}R^{5″})(OR^{4″})$, where $R^{4″}$, $R^{5″}$, and $R^{6″}$ are each independently selected in each occurrence from the group consisting of hydrogen, $C_1$-$C_6$ alkyl, $C_3$-$C_8$ cycloalkyl, $C_1$-$C_6$ haloalkyl, optionally substituted phenyl, and optionally substituted phenyl-$C_1$-$C_6$ alkyl.

2. The compound of claim 1, wherein X and Y are taken together to form =$CR^2R^3$.

3. The compound of claim 1, wherein X and Y are taken together to form =$CR^2R^3$, and the carbon-carbon double bond formed thereby is an E-double bond.

4. The compound of claim 1, wherein Z is selected from the group consisting of hydroxy, amino, $C_1$-$C_6$ alkylamino, and nitro.

5. The compound of claim 1, wherein Z' is selected from the group consisting of $C_1$-$C_6$ alkoxy and nitro.

6. The compound of claim 1, wherein Z″ is selected from the group consisting of $C_1$-$C_6$ alkoxy and nitro.

7. The compound of claim 1, wherein X and Y are taken together to form =$CR^2R^3$; and $R^2$ is $C_1$-$C_6$ haloalkyl or aminoalkyl; and $R^1$ is hydrogen.

8. The compound of claim 1, wherein $R^B$ represents 2-4 substituents where 2 of the substituents are adjacent substituents and are taken together with the attached carbons to form an heterocycle selected from the group consisting of dioxolane and dioxane.

9. The compound of claim 1, wherein $R^B$ represents 2-4 substituents where 2 of said substituents are adjacent substituents and are taken together with the attached carbons to form an optionally substituted heterocycle; and Z″ is selected from the group consisting of $C_1$-$C_6$ alkoxy and nitro.

10. The compound of claim 1, wherein Q is oxygen; and $R^A$ is 2,3-bis($C_1$-$C_6$ alkoxy).

11. The compound of claim 1, wherein Q is oxygen; and $R^1$ is $C_1$-$C_6$ alkyl, aminoalkyl, or $C_1$-$C_6$ haloalkyl.

12. The compound of claim 1, wherein Q is oxygen, $R^A$ is 2,3-bis($C_1$-$C_6$ alkoxy), $R^B$ is 8,9-alkylenedioxy and X and Y are taken together to form $CR^2R^3$, where $R^2$ is hydrogen.

13. The compound of claim 1, wherein Q is oxygen, $R^A$ is 2,3-bis($C_1$-$C_6$ alkoxy), $R^B$ is 8,9-alkylenedioxy, X and Y are taken together to form =$CR^2R^3$, $R^2$ is hydrogen, and $R^1$ is hydrogen, $C_1$-$C_6$ alkyl, $C_3$-$C_8$ cycloalkyl, $C_1$-$C_6$ haloalkyl, $C_3$-$C_8$ halocycloalkyl, amino-$C_1$-$C_6$ alkyl, $C_1$-$C_6$ alkylamino-$C_1$-$C_6$ alkyl, or ($C_1$-$C_6$ alkyl)($C_1$-$C_6$ alkyl)amino-$C_1$-$C_6$ alkyl.

14. A pharmaceutical composition comprising a compound of claim 1 and a pharmaceutically acceptable carrier, excipient, or diluent therefor.

15. A method for treating a mammal in need of relief from cancer, comprising administering to the mammal an effective amount of a compound according to claim 1.

16. A compound of the formula:

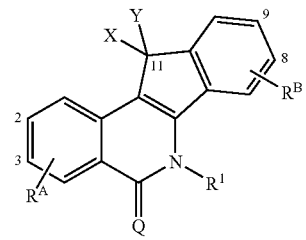

wherein

Q is oxygen or sulfur;

X is hydrogen and Y is $CHR^2R^3$, $NHR^2$, $NHOR^2$, or $NHNR^2R^3$; or X and Y are taken together to form =$CR^2R^3$; =$NR^2$; =$NOR^2$; or =$NNR^2R^3$;

$R^1$, $R^2$, and $R^3$ are each independently selected from the group consisting of hydrogen and a radical —$(CH_2)_mZ$, where m is an integer from 0-6 and Z is selected from the group consisting of halogen, hydroxy, formyl, $C_1$-$C_6$ alkanoyloxy, optionally substituted benzoyloxy, $C_1$-$C_6$ alkyl, $C_1$-$C_6$ alkoxy, $C_3$-$C_8$ cycloalkyl, $C_3$-$C_8$ cycloalkoxy, $C_2$-$C_6$ alkenyl, $C_2$-$C_6$ alkynyl, $C_1$-$C_6$ haloalkyl, $C_1$-$C_6$ haloalkoxy, $C_3$-$C_8$ halocycloalkyl, $C_3$-$C_8$ halocycloalkoxy, amino, $C_1$-$C_6$ alkylamino, ($C_1$-$C_6$ alkyl)($C_1$-$C_6$ alkyl)amino, alkylcarbonylamino, N—($C_1$-$C_6$ alkyl)alkylcarbonylamino, aminoalkyl, $C_1$-$C_6$ alkylaminoalkyl, ($C_1$-$C_6$ alkyl)($C_1$-$C_6$ alkyl)aminoalkyl, alkylcarbonylaminoalkyl, N—($C_1$-$C_6$alkyl)alkylcarbonylaminoalkyl, cyano, nitro, $C_1$-$C_6$ alkylsulfonyl, optionally substituted phenyl, optionally substituted phenoxy, and optionally substituted heteroaryl; or Z is selected from the group consisting of —$N_3$, —$CO_2R^4$, —$CONR^5R^6$, —$P(O)(OR^4)_2$, —$P(O)(NR^4R^5)_2$, and —$P(O)(NR^4R^5)(OR^4)$, where $R^4$, $R^5$, and $R^6$ are each independently selected in each occurrence from the group consisting of hydrogen, $C_1$-$C_6$ alkyl, $C_3$-$C_5$ cycloalkyl, $C_1$-$C_6$ haloalkyl, optionally substituted phenyl, and optionally substituted phenyl-$C_1$-$C_6$ alkyl; or when X and Y are taken together to form =$NNR^2R^3$, $R^2$ and $R^3$ are taken together with the attached nitrogen to form an optionally substituted heterocycle;

providing that Y and $R^1$ are not both alkyl;

$R^A$ represents 1-4 substituents each independently selected from the group consisting of hydrogen and a radical —$(CH_2)_{m'}Z'$, where m' is an integer from 0-6 and Z' is selected from the group consisting of halogen, hydroxy, $C_1$-$C_6$ alkanoyloxy, optionally substituted benzoyloxy, $C_1$-$C_6$ alkyl, $C_1$-$C_6$ alkoxy, $C_3$-$C_8$ cycloalkyl, $C_3$-$C_8$ cycloalkoxy, $C_2$-$C_6$ alkenyl, $C_2$-$C_6$ alkynyl, $C_1$-$C_6$ haloalkyl, $C_1$-$C_6$ haloalkoxy, $C_3$-$C_8$ halocycloalkyl, $C_3$-$C_8$ halocycloalkoxy, amino, $C_1$-$C_6$ alkylamino, ($C_1$-$C_6$ alkyl)($C_1$-$C_6$ alkyl)amino, alkylcarbonylamino, N—($C_1$-$C_6$ alkyl)alkylcarbonylamino, aminoalkyl, $C_1$-$C_6$ alkylaminoalkyl, ($C_1$-$C_6$ alkyl)($C_1$-$C_6$ alkyl)aminoalkyl, alkylcarbonylaminoalkyl, N—($C_1$-$C_6$ alkyl)alkylcarbonylaminoalkyl, cyano, nitro, $C_1$-$C_6$ alkylsulfonyl, optionally substituted phenyl, optionally substituted phenoxy, and optionally substituted heteroaryl; or Z' is selected from the group consisting of —$N_3$, —$CO_2R^{4'}$, —$CONR^{5'}R^{6'}$, —$P(O)(OR^{4'})_2$, —$P(O)(NR^{4'}R^{5'})_2$, and —$P(O)(NR^{4'}R^{5'})(OR^{4'})$, where $R^{4'}$, $R^{5'}$, and $R^{6'}$ are each independently selected in each occurrence from the group consisting of hydrogen, $C_1$-$C_6$ alkyl, $C_3$-$C_8$ cycloalkyl, $C_1$-$C_6$ haloalkyl, optionally substituted phenyl, and optionally substituted phenyl-$C_1$-$C_6$ alkyl; or $R^A$ represents 2-4 substituents where 2 of said substituents are adjacent substituents and are taken together with the attached carbons to form an optionally substituted carbocycle or an optionally substituted heterocycle, and the remaining 2 substituents are each independently selected from the group consisting of hydrogen and a radical —$(CH_2)_{m'}Z'$, where m' is an integer from 0-6 and Z' is selected from the group consisting of halogen, hydroxy, $C_1$-$C_6$ alkanoyloxy, optionally substituted benzoyloxy, $C_1$-$C_6$ alkyl, $C_1$-$C_6$ alkoxy, $C_3$-$C_8$ cycloalkyl, $C_3$-$C_8$ cycloalkoxy, $C_2$-$C_6$ alkenyl, $C_2$-$C_6$ alkynyl, $C_1$-$C_6$ haloalkyl, $C_1$-$C_6$ haloalkoxy, $C_3$-$C_8$ halocycloalkyl, $C_3$-$C_8$ halocycloalkoxy, amino, $C_1$-$C_6$ alkylamino, ($C_1$-$C_6$ alkyl)($C_1$-$C_6$ alkyl)amino, alkylcarbonylamino, N—($C_1$-$C_6$ alkyl)alkylcarbonylamino, aminoalkyl, $C_1$-$C_6$ alkylaminoalkyl, ($C_1$-$C_6$ alkyl)($C_1$-$C_6$ alkyl)aminoalkyl, alkylcarbonylaminoalkyl, N—($C_1$-$C_6$ alkyl)alkylcarbonylaminoalkyl, cyano, nitro, $C_1$-$C_6$ alkylsulfonyl, optionally substituted phenyl, optionally substituted phenoxy, and optionally substituted heteroaryl; or Z' is selected from the group consisting of —$N_3$, —$CO_2R^{4'}$, —$CONR^{5'}R^{6'}$, —$P(O)(OR^{4'})_2$, —$P(O)(NR^{4'}R^{5'})_2$, and —$P(O)(NR^{4'}R^{5'})(OR^{4'})$, where $R^{4'}$, $R^{5'}$, and $R^{6'}$ are each independently selected in each occurrence from the group consisting of hydrogen, $C_1$-$C_6$ alkyl, $C_3$-$C_8$ cycloalkyl, $C_1$-$C_6$ haloalkyl, optionally substituted phenyl, and optionally substituted phenyl-$C_1$-$C_6$ alkyl; and $R^B$ represents 2-4 substituents where 2 of said substituents are adjacent substituents and are taken together with the attached carbon atoms to form an optionally substituted heterocycle and the remaining 2 substituents are each independently selected from the group consisting of hydrogen and a radical —$(CH_2)_{m''}Z''$, where m'' is an integer from 0-6 and Z'' is selected from the group consisting of halogen, hydroxy, $C_1$-$C_6$ alkanoyloxy, optionally substituted benzoyloxy, $C_1$-$C_6$ alkyl, $C_1$-$C_6$ alkoxy, $C_3$-$C_8$ cycloalkyl, $C_3$-$C_8$ cycloalkoxy, $C_2$-$C_6$ alkenyl, $C_2$-$C_6$ alkynyl, $C_1$-$C_6$ haloalkyl, $C_1$-$C_6$ haloalkoxy, $C_3$-$C_8$ halocycloalkyl, $C_3$-$C_8$ halocycloalkoxy, amino, $C_1$-$C_6$ alkylamino, ($C_1$-$C_6$ alkyl)($C_1$-$C_6$ alkyl)amino, alkylcarbonylamino, N—($C_1$-$C_6$ alkyl)alkylcarbonylamino, aminoalkyl, $C_1$-$C_6$ alkylaminoalkyl, ($C_1$-$C_6$ alkyl)($C_1$-$C_6$ alkyl)aminoalkyl, alkylcarbonylaminoalkyl, N—($C_1$-$C_6$ alkyl)alkylcarbonylaminoalkyl, cyano, nitro, $C_1$-$C_6$ alkylsulfonyl, optionally substituted phenyl, optionally substituted phenoxy, and optionally substituted heteroaryl; or Z'' is selected from the group consisting of —$N_3$, —$CO_2R^{4''}$, —$CONR^{5''}R^{6''}$, —$P(O)(OR^{4''})_2$, —$P(O)(NR^{4''}R^{5''})_2$, and —$P(O)(NR^{4''}R^{5''})(OR^{4''})$, where $R^{4''}$, $R^{5''}$, and $R^{6''}$ are each independently selected in each occurrence from the group consisting of hydrogen, $C_1$-$C_6$ alkyl, $C_3$-$C_8$ cycloalkyl, $C_1$-$C_6$ haloalkyl, optionally substituted phenyl, and optionally substituted phenyl-$C_1$-$C_6$ alkyl.

17. The compound of claim 16, wherein the heterocycle is selected from the group consisting of dioxolane and dioxane.

18. The compound of claim 16, wherein Z is selected from the group consisting of hydroxy, amino, $C_1$-$C_6$ alkylamino, and nitro.

19. The compound of claim 16, wherein Z' is selected from the group consisting of $C_1$-$C_6$ alkoxy and nitro.

* * * * *

UNITED STATES PATENT AND TRADEMARK OFFICE
CERTIFICATE OF CORRECTION

PATENT NO. : 7,312,228 B2
APPLICATION NO. : 10/553532
DATED : December 25, 2007
INVENTOR(S) : Mark S. Cushman and Yves G. Pommier It is certified that error appears in the above-identified patent and that said Letters Patent is hereby corrected as shown below:

in Column 22, line 1 replace "$(OR_{4'})$" with --$(OR^{4'})$-- in Column 23, line 53 replace "form $CR^2R^3$" with --form $=CR^2R^3$--

Signed and Sealed this

Twenty-ninth Day of April, 2008

JON W. DUDAS
*Director of the United States Patent and Trademark Office*